(12) United States Patent
Cheng et al.

(10) Patent No.: US 11,504,030 B2
(45) Date of Patent: Nov. 22, 2022

(54) METHOD AND SYSTEM FOR HETEROGENEOUS EVENT DETECTION

(71) Applicant: ORPYX MEDICAL TECHNOLOGIES INC., Calgary (CA)

(72) Inventors: Chun Hing Cheng, Calgary (CA); Michael Todd Purdy, Calgary (CA); Travis Michael Stevens, Calgary (CA)

(73) Assignee: ORPYX MEDICAL TECHNOLOGIES INC., Calgary (CA)

(*) Notice: Subject to any disclaimer, the term of this patent is extended or adjusted under 35 U.S.C. 154(b) by 345 days.

(21) Appl. No.: 16/623,475

(22) PCT Filed: Jun. 28, 2018

(86) PCT No.: PCT/CA2018/050802
§ 371 (c)(1),
(2) Date: Dec. 17, 2019

(87) PCT Pub. No.: WO2019/000100
PCT Pub. Date: Jan. 3, 2019

(65) Prior Publication Data
US 2020/0178849 A1 Jun. 11, 2020

Related U.S. Application Data

(60) Provisional application No. 62/574,013, filed on Oct. 18, 2017, provisional application No. 62/526,080, filed on Jun. 28, 2017.

(51) Int. Cl.
*A61B 5/11* (2006.01)
*A43B 17/00* (2006.01)
(Continued)

(52) U.S. Cl.
CPC ............ *A61B 5/112* (2013.01); *A43B 17/00* (2013.01); *A61B 5/1036* (2013.01);
(Continued)

(58) Field of Classification Search
CPC ..... A61B 5/112; A61B 5/1036; A61B 5/1116; A61B 5/1118; A61B 5/1123;
(Continued)

(56) References Cited

U.S. PATENT DOCUMENTS 9,418,705 B2  8/2016  Kaps et al.
9,459,118 B2  10/2016  Pham et al.
(Continued)

OTHER PUBLICATIONS

Stockwell, R.G., 2007. A basis for efficient representation of the S-transform Digital Signal Processing, 17, pp. 371 393. (Year: 2007).*

(Continued)

*Primary Examiner* — Matthew Kremer
*Assistant Examiner* — Alyssa N Potter
(74) *Attorney, Agent, or Firm* — ABM Intellectual Property Inc.; Adrienne Bieber McNeil

(57) ABSTRACT

A method and system for heterogeneous event detection. Sensor data is obtained and divided into discrete data windows. Each data window is defined by and corresponds to a time period of the sensor data. A time-frequency representation over the time period is calculated for each data window. A filter mask is calculated based on the data window corresponding to the time-frequency representation. The filter mask is applied for reverting the time-frequency representation to a time representation, resulting in filtered data. Features, such as extrema or other inflection points, are identified in the filtered data. The features define events, and transforming the time-frequency representation back into the time domain emphasizes differences between more and (Continued)

less prominent frequencies, facilitating identification of heterogeneous events. The method and system may be applied to body movements of people or animals, automaton movement, audio signals, light intensity, or any suitable time-dependent variable.

19 Claims, 28 Drawing Sheets

(51) Int. Cl.
    *A61B 5/00*         (2006.01)
    *A61B 5/103*       (2006.01)

(52) U.S. Cl.
    CPC .......... *A61B 5/1116* (2013.01); *A61B 5/1118* (2013.01); *A61B 5/1123* (2013.01); *A61B 5/1126* (2013.01); *A61B 5/6807* (2013.01); *A61B 5/725* (2013.01); *A61B 5/7253* (2013.01); *A61B 5/7264* (2013.01); *A61B 5/7282* (2013.01)

(58) Field of Classification Search
    CPC ..... A61B 5/1126; A61B 5/6807; A61B 5/725; A61B 5/7253; A61B 5/7264; A61B 5/7282; A43B 17/00
    See application file for complete search history.

(56) References Cited

U.S. PATENT DOCUMENTS

2013/0085700 A1*   4/2013   Modi ................... G01C 22/006
                                                        702/104
2016/0029968 A1    2/2016   Lerner et al.

OTHER PUBLICATIONS

Wilczok, Elke. "New Uncertainty Principles for the Continuous Gabor Transform and the Continuous Wavelet Transform." Documenta Mathematica 5, 2000, pp. 201-226. (Year: 2000).*
International Search Report, Search Strategy, and Written Opinion of the International Searching Authority International Application No. PCT/CA2018/050802; dated Oct. 4, 2018.

* cited by examiner

METHOD AND SYSTEM FOR HETEROGENEOUS EVENT DETECTION

CROSS REFERENCE TO RELATED APPLICATIONS

This application is a national stage entry of International Patent Application Number PCT/CA2018/050802 filed Jun. 28, 2018 and entitled "METHOD AND SYSTEM FOR HETEROGENEOUS EVENT DETECTION", which claims the benefit of priority of U.S. Provisional Patent Application No. 62/526,080 filed Jun. 28, 2017 and of U.S. Provisional Patent Application No. 62/574,013, filed Oct. 18, 2017, each entitled "METHOD AND SYSTEM FOR HETEROGENEOUS EVENT DETECTION", and each of which is incorporated herein by reference in its entirety.

FIELD

The present disclosure relates to heterogeneous event detection.

BACKGROUND

Human motion, such as walking, running, and jumping, may be characterized as a series of separate events with generally predictable trends, such as plantar pressure at the end of a step and acceleration of a foot through a step. Counting such events within a period of time to monitor activity levels may have application in fitness, healthcare, or other contexts. To count such events, wearable sensors, such as accelerometers, may be strapped onto an individual's wrist, foot, or core. Similarly, pressure or other sensors may be fitted into an insole of a shoe. Time-based data from these sensors may be applied to event detection and characterization.

In some cases, sensor readings may not come in the form of simple waveforms. Activities, particularly those performed by people in motion, are not always regular, and automated analysis of the resulting data sets may not be straightforward. Identifying individual steps or other events may be complicated due to irregularity of motion and the signal-to-noise ratio that may accompany sensing and data transmission. Sensor data of a single step may include several local maxima and minima. Successive steps may differ in speed and pace of the steps, and in intensity of the landing (e.g. light, heavy). Moreover, a person may perform heterogeneous activities, for instance, first walking for a number of steps, followed by running for a number of steps, tapping their feet, jumping, and resuming walking, walking on stairs or a ramp, or any number of other activities.

Many step-detection systems include a processor programmed to analyze time-based sensor data series and identify a step based on peaks and troughs. Smoothing may be employed to eliminate noise effects, thresholds may be applied to discard small peaks or troughs, and enveloping may be applied for reducing data variation. Previous methods may apply a low pass filter or other approach with predetermined threshold parameters, which are in many cases set arbitrarily, and on an underlying assumption that the user is performing only an identified activity that will result in a consistent data profile on each occurrence.

SUMMARY

In view of the shortcomings of some previous approaches to event detection, it is desirable to provide an event detection method for heterogeneous events. In previous approaches, a low-pass Fourier transform or other filter is applied to sensor data series to capture the low-frequency component, which may result in a filtered data series that will show discrete events more definitively. However, a low-pass filter with a single cut-off frequency for an entire data set may not accurately detect events that vary in duration, events that vary in amplitude, events separated by variable amounts of time, or other heterogeneous activities.

Herein provided are a method and system for heterogeneous event detection. The method includes, and the system facilitates, acquiring data from sensors and processing the resulting sensor data to define events that are heterogeneous from occurrence to occurrence of the event. The method and system apply localized adaptive filtering through a local time-frequency transform, an inverse transform, and an adaptive filter mask. The adaptive filter mask is based on the time-frequency representation and is defined for time periods defining data windows, with reference to locally abundant frequencies. The method and system provide an adaptive approach that may be applied to detecting events that can be predicted in terms of trends in sensor data associated with the event, but that may not be consistent from one occurrence of an event to the next.

In applications directed to human movement or interpretation of audio data, trends such as plantar pressure following a step or other change in weight distribution on feet, acceleration or rotation during a step or other body movement, or changes in amplitude or frequency of a sound or collection of sounds may all be indicative of events that are generally predictable but that do not result in identical data on each occurrence. The events may be generally repetitive or recurring. In response to the event, the method and system may prompt a suggested change to improve performance of the event or outcome of the event. In response to the event, the method and system may update parameters of how the event is characterized or change parameters of how a device functions to change user experience in relation to the event or prepare for an outcome expected to follow the event.

The method and system may be applied continuously, in real-time or in batch processing. The method and system may be applied using a pressure sensor, a gyroscope, an accelerometer, a thermometer, a humidity sensor or any suitable sensor or combination of sensors depending on the specific application. The method and system may be applied to detecting events that are steps or other defined body movements associated with various activities (e.g. walking, running, jumping, biking, skiing, swimming, martial arts, boxing, yoga, gymnastics, dancing, etc.), or portions of any such activities. The method and system may be applied to use on individuals, animals, robotics, unmanned or manned vehicles, or any suitable system. The method and system may be applied to optimize activities of a user or test subject, including by prompting changes (e.g. audio, visual or tactile alerts to change movement patterns), or by changing device function (e.g. by inflating or deflating bladders around an insole, changing stiffness of wrist or other joint braces, changing output from a hearing aid, etc.).

Applying the localized adaptive filter to the sensor data may include segmenting the sensor data into data windows and converting the resulting data windows into a time-frequency representation using a transform such as the S-transform. In the time-frequency representation, the relative contributions of many frequencies of the sensor data profile can be represented for each time point. Adaptive localized filtering magnifies the most prominent frequencies at each time point and suppresses the least prominent frequencies in the resulting filtered data. The adaptive filtering may be based on a power of the magnitude of the time-frequency representation, resulting in greater divergence in contribution from more prominent frequencies as compared with less prominent frequencies. The greater divergence in contribution from more prominent frequencies as compared with less prominent frequencies may facilitate heterogeneous event detection.

The adaptive localized filtering provides filtered data. Identifying events is facilitated in features of the filtered data compared with features of the sensor data. Once the events are identified along the timeline of the filtered data, the events may be further characterized in either the filtered data or the sensor data. Characterization along the timeline of either the filtered data or the sensor data may include analysis of the derivative or the integral of the data.

In a first aspect, herein provided is a method and system for heterogeneous event detection. Sensor data is obtained and divided into discrete data windows. Each data window is defined by and corresponds to a time period of the sensor data. A time-frequency representation over the time period is calculated for each data window. A filter mask is calculated based on the data window corresponding to the time-frequency representation. The filter mask is applied for reverting the time-frequency representation to a time representation, resulting in filtered data. Features, such as extrema or other inflection points, are identified in the filtered data. The features define events, and transforming the time-frequency representation back into the time domain emphasizes differences between more and less prominent frequencies, facilitating identification of heterogeneous events. The method and system may be applied to body movements of people or animals, automaton movement, audio signals, light intensity, or any suitable time-dependent variable.

In a further aspect, herein provided is a method for detecting heterogeneous events related to movement of an individual comprising: receiving sensor data of movement of the individual; defining a data window over a time period of the sensor data; calculating a time frequency-representation of the data window for providing a time-frequency representation corresponding to the time period; calculating a filter mask based on the time-frequency representation; filtering the time-frequency representation with the filter mask, providing filtered data; identifying features in the filtered data; identifying an event with reference to the features; and outputting the event.

In a further aspect, herein provided is a method for detecting heterogeneous events comprising: receiving sensor data; defining a data window over a time period of the sensor data; calculating a time frequency-representation of the data window for providing a time-frequency representation corresponding to the time period; calculating a filter mask based on the time-frequency representation; filtering the time-frequency representation with the filter mask, providing filtered data; identifying features in the filtered data; identifying an event with reference to the features; and outputting the event.

In a further aspect, herein provided is system for detecting heterogeneous events comprising: a sensor for receiving sensor data; and a processor in communication with the sensor for receiving the sensor data; wherein the processor is configured to execute instructions for carrying out the methods described above.

In some embodiments of the methods and systems, the sensor data comprises at least two different types of data; the sensor data comprises data of pressure, acceleration, rotation, seismic changes, temperature, humidity, or sound; receiving the sensor data is at a down-sampled rate to increase event detection speed; receiving the sensor data of a first data window is at a rate determined with reference to the filtered data of a second data window, the second data window preceding the first data window in time; the time period of the data window has a duration equal to additional data windows preceding or succeeding the data window; calculating a time frequency-representation of the data window comprises applying an S-transform to the sensor data within the data window; filtering the time-frequency representation with the filter mask comprises applying the filter mask to the time-frequency representation and applying the inverse S-transform to the product of the filter mask and the time-frequency representation; applying the filter mask to the S-transform comprises multiplying the time-frequency representation by the filter mask; calculating a time frequency-representation of the data window comprises applying a Gabor transform to the sensor data within the data window; filtering the time-frequency representation with the filter mask comprises applying the filter mask to the time-frequency representation and applying the inverse Gabor transform to the product of the filter mask and the time-frequency representation; filter mask to the Gabor transform comprises multiplying the time-frequency representation by the filter mask; the filter mask comprises non-binary values proportional to a positive exponent of the magnitude of the time-frequency transform, wherein more prominent frequencies will be emphasized, and less prominent frequencies will be de-emphasized; the exponent is 1; the exponent is 2; filtering the time-frequency representation comprises normalizing all values in the time-frequency representation; the features comprise inflection points; at least one inflection point of the inflection points comprises a local extremum; identifying the inflection points comprises identifying at least one inflection point of the inflection points within a first data window based on at least one inflection point of a second data window, the second data window preceding the first data window in time. identifying the event comprises deriving an event count; identifying the event comprises defining the features as endpoints of the event; identifying the event comprises characterizing the sensor data between time points corresponding to the endpoints defined in the filtered data; characterizing the sensor data comprises deriving the sensor data; characterizing the sensor data comprises integrating the sensor data; identifying the event comprises characterizing the filtered data between the endpoints; characterizing the filtered data comprises deriving the filtered data; characterizing the filtered data comprises integrating the filtered data; identifying the event comprises defining a pulse width, a cycle, a ground contact time, a center of pressure, or a path of center of pressure of the sensor data or the filtered data; outputting the event comprises communicating data relating to the event to an individual; outputting the event comprises prompting an individual to change behavior; outputting the event comprises communicating data relating to the event to an individual; outputting the event comprises storing data relating to the event in a computer readable medium; outputting the event comprises outputting contribution to the sensor data from each of a plurality of sensors; or any of the foregoing.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures, in which reference numerals having a common final two digits refer to corresponding features across figures (e.g. the method 50, method 150, etc.).

DETAILED DESCRIPTION

Figure 1:
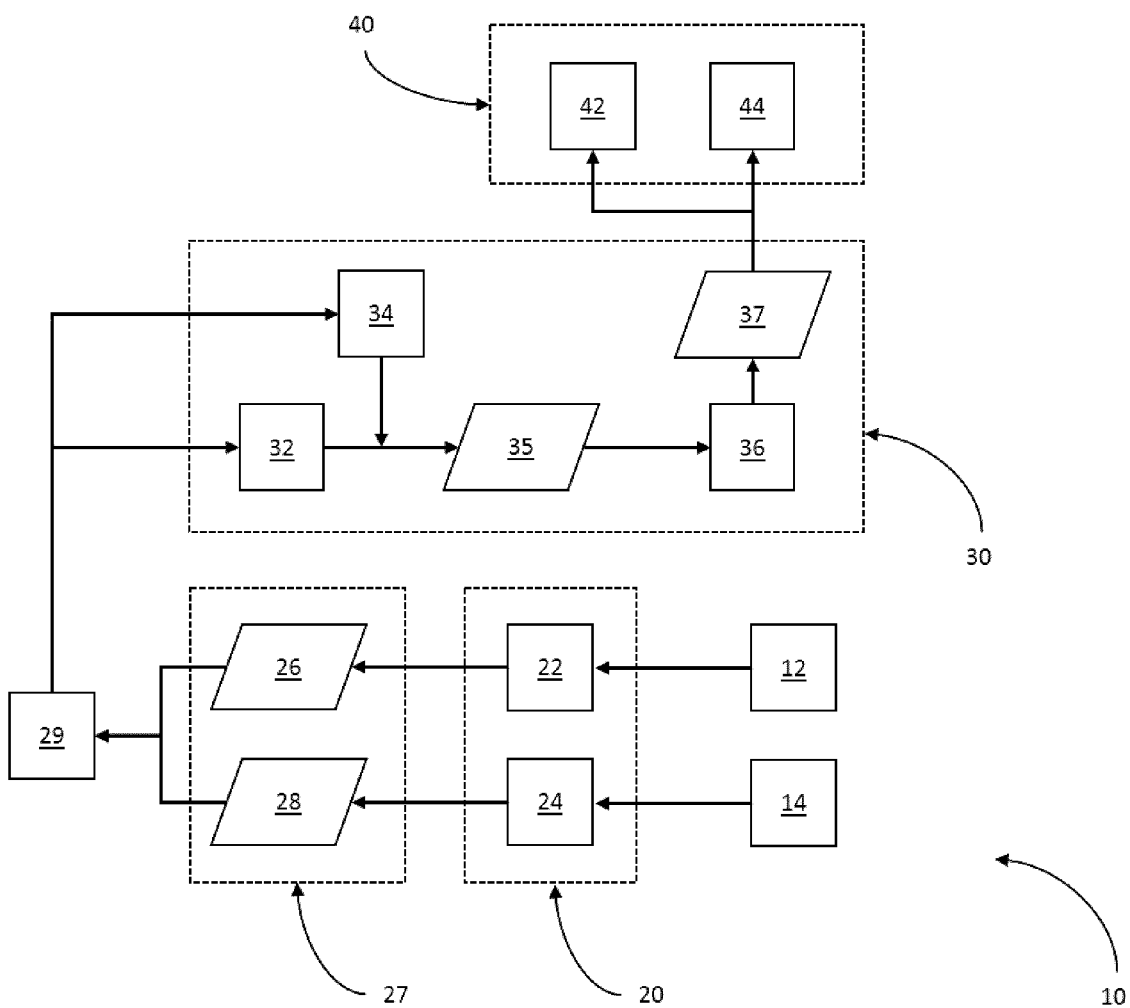
FIG. 1 is a block diagram of an event detection system.

Herein provided are a method and system for heterogeneous event detection. The method includes, and the system facilitates, acquiring data from sensors and processing the resulting sensor data to define events that are heterogeneous from occurrence to occurrence of the event. The method and system apply localized adaptive filtering through a local time-frequency transform, an inverse transform, and an adaptive filter mask. The adaptive filter mask is based on the time-frequency representation and is defined for time periods defining data windows, with reference to locally abundant frequencies. The method and system provide an adaptive approach that may be applied to detecting events in real-time or in batch processing. The filter mask is determined with respect to local conditions around an event, avoiding the need for arbitrary thresholds, which are applied in many other commonly used detection techniques. The method and system provide a robust and adaptive solution for detecting movements of people, animal or automata, detecting sounds, or any receive data associated with any other type of event that may not be consistent from one occurrence of the event to the next.

Each individual event may be characterized and characteristics of the event may be defined. The characteristics may be used to analyze the sensor data for characteristics that may include duty cycles of events and statistics surrounding the characteristics. Event detection may be facilitated by identifying characteristics within the event other than the duration and boundaries of the event. Such characteristics may include the pulse width of each event, the contribution from multiple sensors during an event, and the duty cycle if the events are periodic. These characteristics describe the event, and may be used to verify the event detection process. The characteristics may be provided to a user of the method and system as event data. In response to the event, the method and system may prompt a suggested change to improve performance of the event or outcome of the event. In response to the event and the event data, the method and system may update parameters of how the event is characterized or change parameters of how a device functions to change user experience in relation to the event or prepare for an outcome expected to follow the event.

Applying the localized adaptive filter to the sensor data may include segmenting the sensor data into data windows and converting the resulting data windows into a time-frequency representation using a transform such as the S-transform, including a discretized S-transform. In the time-frequency representation, the relative contributions of many frequencies of the sensor data profile can be represented for each time point. Adaptive localized filtering magnifies the most prominent frequencies at each time point and suppresses the least prominent frequencies at each time point in the resulting filtered data. The adaptive filtering may be based on a power of the magnitude of the time-frequency representation, resulting in greater divergence in contribution from more prominent frequencies as compared with less prominent frequencies. The greater divergence in contribution from more prominent frequencies as compared with less prominent frequencies may facilitate heterogeneous event detection.

Generally, an event is defined as a distinct waveform bound between two features along the timeline of the sensor data or filtered data, although as described above, locating the features is facilitated in the filtered data relative to locating the features the sensor data. The features may include inflection points. The inflection points may be local extrema within the data, a derivative of the data, or an integral of the data. Once an event has been delineated in the filtered data, further processing of the event within its boundaries may be performed with reference to the filtered data, the sensor data or both. A portion of the event that occurs above a predefined threshold in respect of sensor data from one or more sensors may define a shape or other characteristic of the event. One method of describing the event is by its pulse width, which is the amount of time that the sensor data of the event is above a specified threshold, typically beyond a baseline level in a data series. The pulse width is defined as the timeline between the start and end times of an event. Sensor contribution can be studied within the pulse width. Definition of these characteristics facilitates detection and analysis of events, and of other aspects of the data set.

Event detection acts as a preliminary step in analyzing input data. Generally, the information of interest in a data set includes dynamic events rather than the static moments. Once an event is detected and delineated, the event may be further analyzed. Analysis of the event and of features within the event is not possible without first detecting the event. An event of interest may be heterogeneous in nature, consisting of repetitive or non-repetitive occurrences. In the case of repetitive, reoccurring events, there may be high or low variability from event to event.

The method and system may be applied to detecting events that are not consistent from one occurrence of the event to the next, and that may occur with inconsistent intervals between occurrences. The method and system may be applied to detecting events that are steps or other defined body movements associated with various activities (e.g. walking, running, jumping, biking, skiing, swimming, martial arts, boxing, yoga, gymnastics, dancing, etc.), or portions of any such activities. The method may include use of, and system may include, sensors that are worn on the feet, legs, wrists, arms, torso or other portions of the body, depending on the application. The sensors may include a pressure sensor, a gyroscope, an accelerometer, a seismograph, a thermometer, a humidity sensor, a microphone or other audio sensor, an optical sensor or any suitable sensor or combination of sensors depending on the specific application. Actuators or other output modules may drive changes in device function following detection.

The method and system may be applied to optimize activities of a user or test subject, including by prompting changes (e.g. audio, visual or tactile alerts to change movement patterns), or by changing device function (e.g. by inflating or deflating bladders around an insole, changing stiffness of wrist or other joint braces, changing output from a hearing aid, etc.). These responses may facilitate improved performance of movements that are detected and characterized as an event. Particularly with application to body movements that are generally repetitive, coaching alerts and changes in device function may improve performance of the physical activity. Audio data may also be used in applications to improve device function, such as changing output from a hearing aid in response to changes in background noise or audio data indicative that a known person is talking and to emphasize or de-emphasize certain frequencies in audio output to help a user hear higher or lower frequencies. Audio data may also prompt changes, for example to improve playing a musical instrument, singing, or speaking a language.

The method and system may be applied to gait analysis of a person, animal, or machine, by first detecting individual steps as events within a gait data set and further analyzing the features of each step event, and the statistics of the overall gait data set. A foot strike analysis may be applied to detecting the position on the foot where striking occurs during running or walking to provide coaching feedback improving gait efficiency, and reducing injury potential. A rate of pronation and supination may be detecting within each step event, allowing for coaching to improve gait efficiency and reduce injury.

In applications directed to detecting steps, footfalls or other body movements of an individual, events that are in turn defined by multiple discrete features may be identified, different types of events based on peaks may be characterized, and plots of the sensor data may be applied contextually to generate the time-frequency representation. These features may facilitate accurate definition of heterogeneous events. In the context of detecting steps or other footfalls of an individual, such heterogeneous events may include changing speed, climbing stairs, walking on a ramp or other incline, tapping feet, or other events that may vary in unpredictable ways between footfalls or other events.

Characteristics of each step may be defined, including the pulse width of the step, which may correlate to the ground contact time, and the center of pressure of the step. The sensor data may be represented by summations of multiple pressure sensors. The summations of the sensor data may be filtered by the heterogeneous event detection system, and the filtered data may be used to detect boundaries of step events based on features in the filtered data. The source data that is filtered to provide the filtered data may include pressure data from one or more sensors, and may also include data of acceleration, rotation, temperature, humidity or other data.

Once the boundaries of the step events have been identified in the filtered data, the time bounds of the step events may be used for further analysis of the sensor data or other data. Within the identified time bounds, the pressure from each of the multiple sensors may be compared to one another for analysis. Within the identified time bounds, sensor data, filtered data or both for humidity, temperature or other aspects of the user's feet may be cross-referenced to the pressure data to more thoroughly characterize the event. Similarly, with pressure data as the principal type of data, acceleration, rotation or tilt data may also be superimposed over the pulsewidth of the event to characterize the event other than by pressure.

When characterizing a series of walking steps, three components may commonly be defined: the number of steps within the series, the ground contact time of each step, and the path of center of pressure of the series. The localized adaptive filtering and identification of features in the filtered data facilitates detecting the start time and end time of each individual step, and the number of steps in the series. The ground contact times may be calculated within the bounds of the start and end times for each step. Within a step, the amount of time that a stance phase endures between swing phases defines a ground contact time. Between the start and end times of a step, inflection points of the rising edge and falling edge of a step, representing the onset and offset of the ground contact time respectively, may be detected by a number of means. The ground contact onset and offset points may then be used as bounds in which to calculate centres of pressure for an individual step, to filter out the pressures that are recorded during the swing phase of the step. Any change in center of pressure measurements over multiple steps may yield the path of center of pressure for the walking data.

Correlating the locations of the sensors relative to an individual's foot when measuring steps or other activities involving steps allows the sensor data recorded by each sensor to be used to define the center of pressure of the entire sensor system at any one instant in time using known center of pressure calculations. Similarly, the path of the center of pressure throughout each event may be determined throughout the entire pressure series. Additional characteristics of the sensor data may be calculated after detection of the step, including any events defined within the step, such as a heel strike event, a forefoot strike event, a ground contact with the ball of the foot event, and a toe-off event, each of which may be grouped into a ground contact event portion of the step event. The ground contact event portion may define stance phase, and the remaining features of the data within a cycle may define a swing phase of each step.

Identified features of the sensor data may be leveraged to analyze the sensor data for characteristics that may include the pulse width, the duty cycle, the ground contact time, the center of pressure of the step, the path of the center of pressure, and other statistics (e.g. mean, deviation, etc.) surrounding the features, and relating to various portions of the step event. Such characteristics of the step events may facilitate assessing the mean and deviation ground contact times, changes in center of pressure, changes in the path of the center of pressure, or other characteristics of a step event. These features of step events may be detected by pressure sensors, accelerometers or any other suitable system for detecting movement of a foot and contact of a sole with a walking surface.

After step detection and characterization of heterogeneous steps, the method and system may include adjusting upstream or downstream aspects of the system's functionality to change how the data is processed. For example, if a series of jumps is detected or the pace of a run increases, the method may increase its sampling rate, while if the user appears to be sitting down, the sampling rate may decrease to save battery life. Functional responses of the system to these changes allow for low-power modes, elongating battery life, while still allowing for high frequency sampling during events in order to provide useful information for users in terms of coaching for avoiding injury, coaching for performance, research or any suitable application.

The method and system may also prompt the user in response to an event. The prompt may be in the form of coaching for athletic performance, to avoid injury or for other reasons. The prompting may be communicated to the user in any manner that is appropriate to the application. Visual, audio or tactile feedback triggered by event detection may provide clear suggestions on how to improve performance or avoid injury. The feedback may be neuroplastic, such as for events detected at a region of interest that has limited or no sensation. Providing a tactile feedback to an area that does have sensation may train the user to intuitively recognize and react to that tactile feedback. For example, pressure, acceleration, rotation and temperature sensors may be placed on the foot of a neuropathic patient who has loss of feeling in their feet. The sensors and system may detect a step and convey a signal depicting the detection of the step to a transducer mounted on the patient's back as a vibrational signal that the patient can feel. The event may also include a spike in temperature that the patient may not be able to feel and recoil from.

In some application, movements may be detected on the user's head, neck, hands, arms, torso, legs, feet or any suitable combination. As with sensors on the feet, sensors elsewhere on the body may include pressure, acceleration, rotation, temperature, humidity or any suitable sensor. The sensors may be grouped for processing data singularly from several sensors, and may be grouped according to the location of sensors on the user's body. In some cases, parallel sets of events are characterized on the same timeline. For example, data relating to pressure, acceleration, rotation, temperature and humidity on a user's arms and hands may be assessed trough a first group of sensors, and data relating to separately to pressure, acceleration, rotation, temperature and humidity on a user's legs and feet may be assessed separately trough a second group of sensors. The first and second groups of sensors may provide data for coaching basketball, football, hockey, soccer, swimming, bicycling or any sport where performance optimization and stress injury may be avoided.

In some applications, the event may also include slipping on a slippery surface, detected by an accelerometer but which the patient may not be able to feel and respond to. To provide fall prediction and prevention, the system may detect small, perhaps unnoticed events by pressure, acceleration and rotation measurements in the foot, leg, and torso. Detection and analysis of these events may provide some insights into fall probability, allowing for feedback to the user to change behaviour and prevent the fall, or to trigger an alarm or notify an emergency contact immediately preceding or following the fall.

The method and system may be directed to detecting background noise, spoken word, musical performance or other audio input data, events may be identified, different types of events based on peaks may be characterized, and plots of the sensor data may be applied contextually to generate the time-frequency representation. These features may facilitate accurate definition of heterogeneous events based on audio data. In the context of a hearing aid application, features such as signal amplitudes at various frequencies may be used to modulate output of the hearing aid to eliminate background noise or focus on a given person speaking. In educational applications, audio input data may characterize musical or language performance and provide coaching on that basis. Audio input data may also be included with step detection or other human performance applications to better characterize events and features. For step detection and musical coaching, both audio data and pressure, acceleration or rotation data may be referenced to avoid injury.

Characteristics of words or passages of music may be defined, including the frequencies and amplitudes of the sounds to detect individual syllables or notes. Relationships between individual syllables or notes may also be characterized to define measures, choruses or other passage of music. Consistency of the words and notes, and consistency of tempo and rhythm, may be characterized. Similarly, background noise may be characterized by amplitudes and known repetitive sounds or white noise to identify an environment or social situation to adjust hearing aid output. Summations of the audio sensor data may be filtered by the heterogeneous event detection system, and the filtered data may be used to detect boundaries of verbal, musical, background noise, physical activity of the user, or other events based on features in the filtered data. The source data that is filtered to provide the filtered data may include audio data from one or more sensors, and may also include data of pressure, acceleration, rotation, temperature, humidity or other data depending on the application.

Once the boundaries of spoken or musical events have been identified in the filtered data, the time bounds of the step events may be used for further analysis of the sensor data or other data. Within the identified time bounds, audio inputs from each of multiple sensors may be compared to one another for analysis, and both the source data and the filtered data may be assessed for identification of heterogeneous events. In the case of musical coaching, the performer's physical posture and the music may be assessed separately to both improve performance and avoid injury.

FIG. 1 shows a system 10 that may be used to implement a method for defining heterogeneous events. The system 10 may include a data source 20 from which a processing module 30 receives and processes data, allowing detection and visualization of heterogeneous events. Downstream functionality of the system 10 in response to data after processing by the processing module 30 is directed by an event data module 40, which may store processed data, communicate processed data to a user or change operating parameters of the system 10 in response to processed data.

The data source 20 may include one or more sensors for receiving data of different types of stimulus. The data source 20 may also include stored data or simulated data for modelling and optimization. The data source 20 shown includes a first sensor 22 and a second sensor 24. A data source may include only the first sensor, such as the data source 420 of FIG. 15. The first sensor 22 receives a first stimulus 12, resulting in the first data 26. The second sensor 24 receives a second stimulus 14, resulting in the second data 28. The first sensor 22 and the second sensor 24 may be the same types of sensors for detecting the same types of data, or may be a combination of multiple types of sensors. The first sensor 22, the second sensor 24, or both, may include a pressure sensor, a gyroscope, an accelerometer, a seismograph, a thermometer, a humidity sensor, or any suitable sensor or combination of sensors depending on the specific application. The first data 26, the second data 28, or both, and correspondingly the first stimulus 12, the second stimulus 14, or both, may include measured pressure, acceleration, rotation, seismic signals, temperature, humidity, or any other data.

Figure 8:
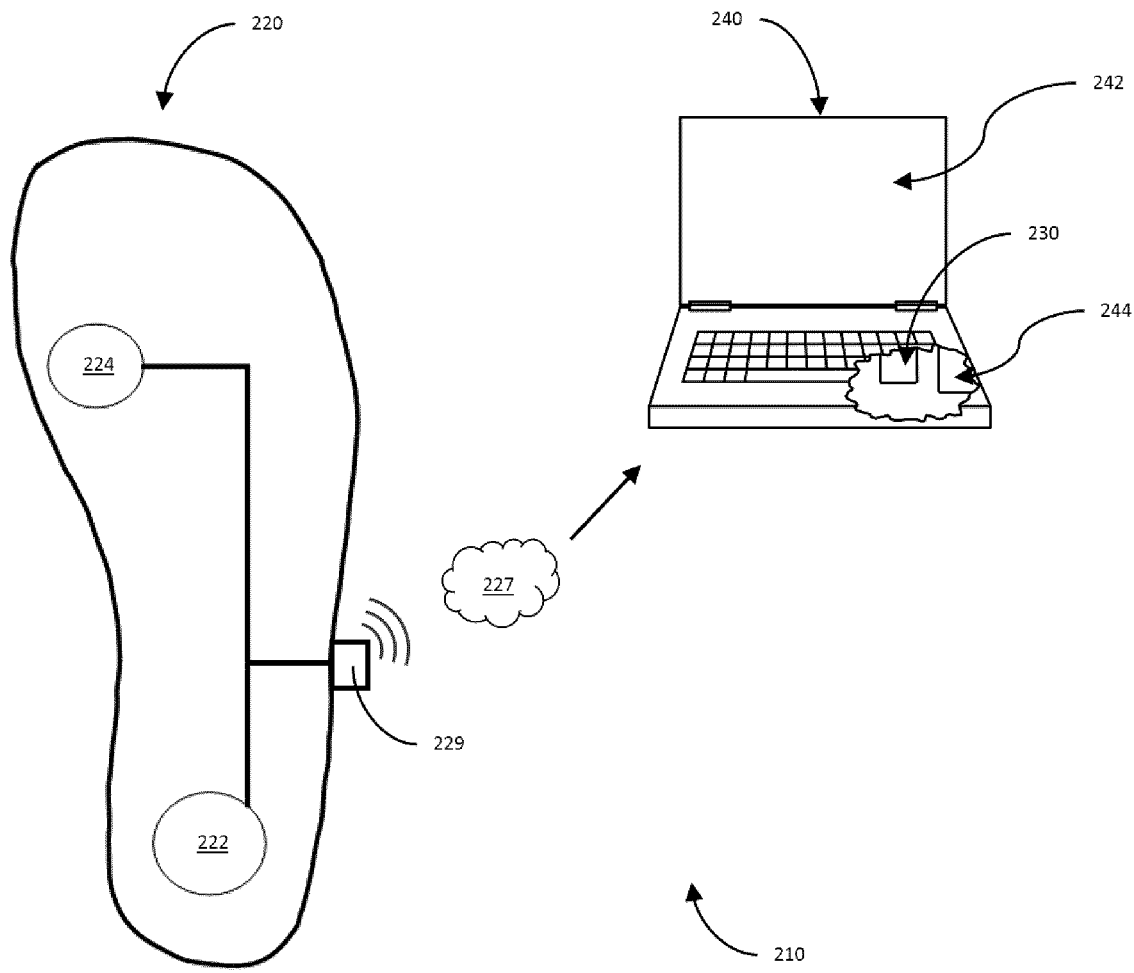
FIG. 8 shows an event detection system.
Figure 13:
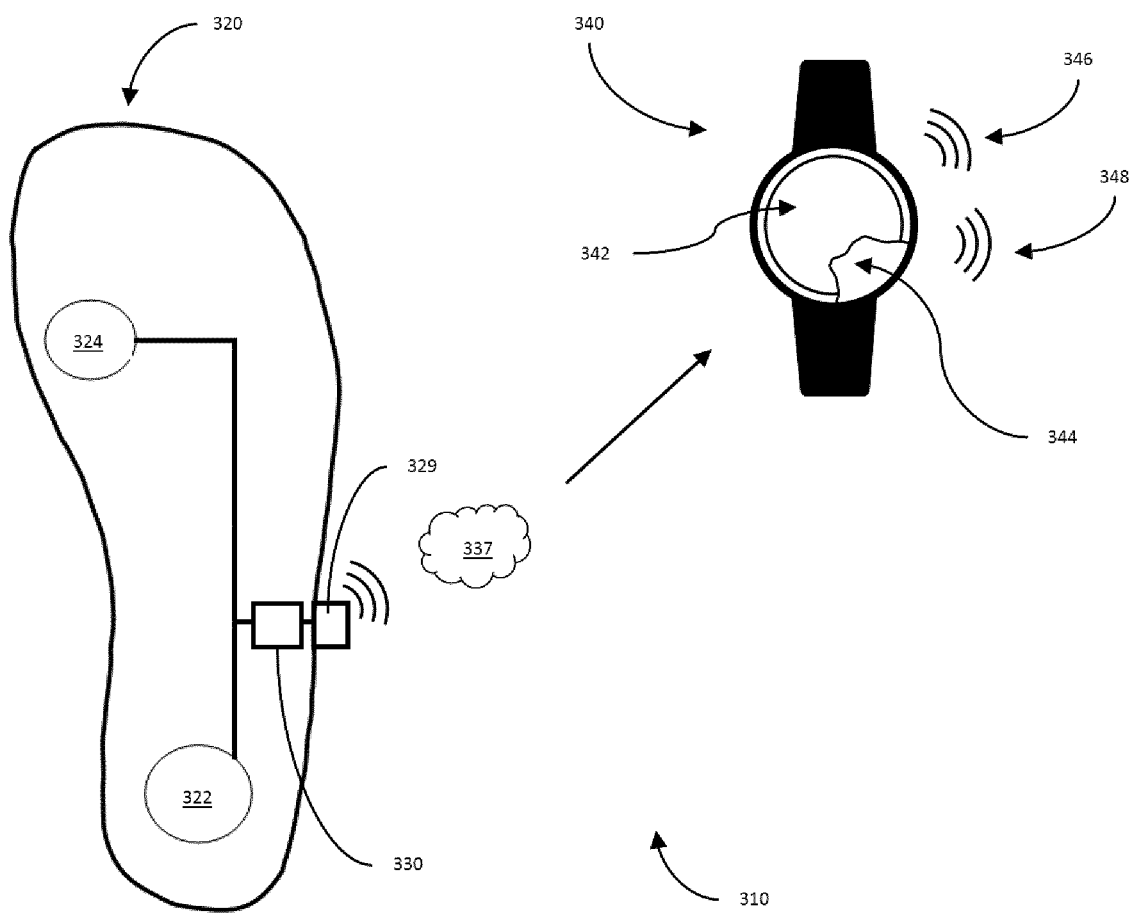
FIG. 13 shows an event detection system.
Figure 15:
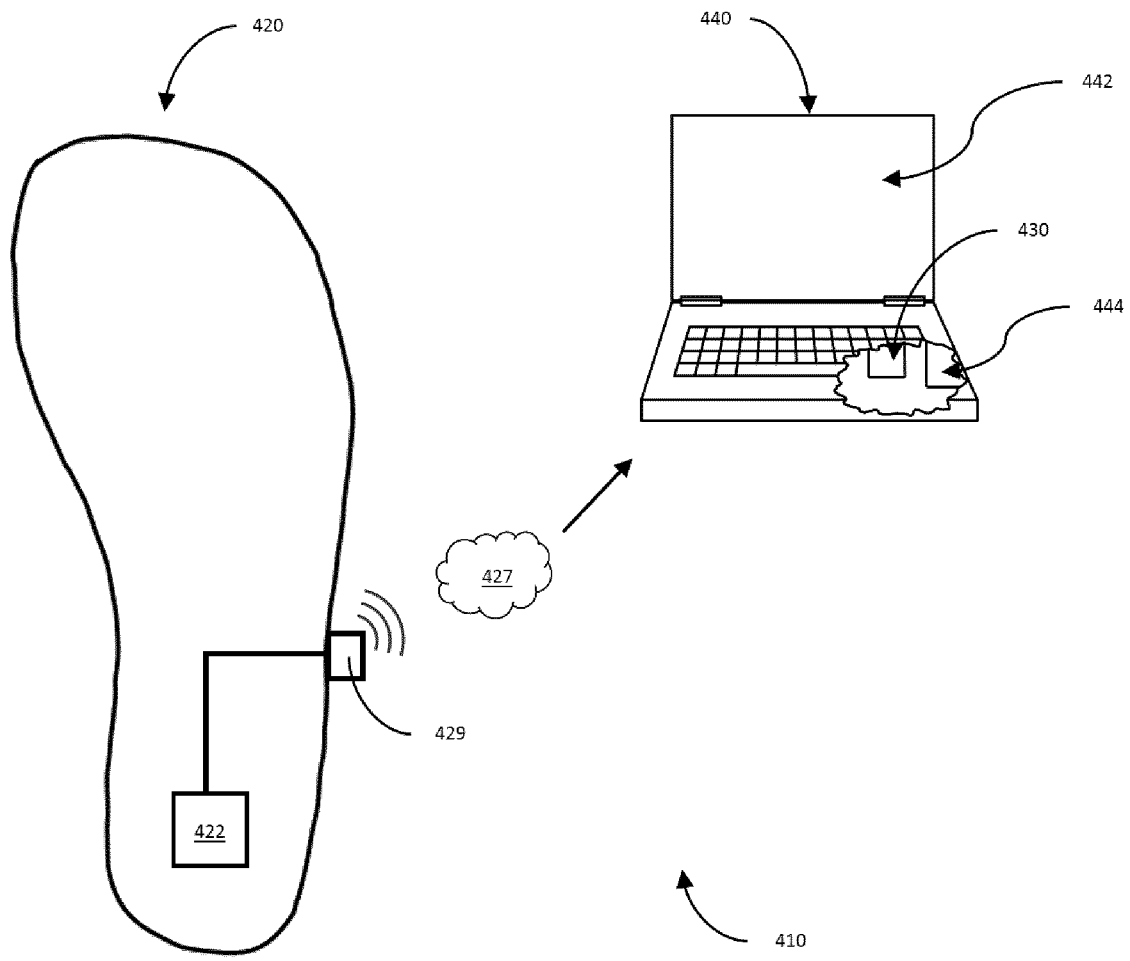
FIG. 15 shows an event detection system.

The data source 20 may include a shoe-insert, such as the data source 220 of FIG. 8, the data source 320 of FIG. 13 or the data source 420 of FIG. 15. A shoe insert facilitates measuring the applied pressure at specific portions of a user's foot during walking, running, jumping, biking, skiing, or other activities. The first sensor 22 and the second sensor 24 may be combined in a sensor array included in the shoe-insert, such as the first sensor 222 and the second sensor 224 of FIG. 8. The data source may include one or more sensors on a glove, wristband, armband, elbow pad, headband, hairclip, torso harness, shirt, halter, belt, earpiece, ankle bracelet, leg band, knee pad, or any suitable location (not shown), any of which may be designed for an individual, an animal, an automaton a prosthetic or any suitable location for a given application. The data source may include one or more sensors on a component of a robotics, unmanned or manned vehicles, or any suitable system. The data source 20 may include a glove, such as the data source 620 of FIG. 20, or any other suitable wearable data source. The data source 20 may also include an audio detection device such as the cochlear implant 620 of FIG. 18. The data source 20 may also include a sensory enhancement device, such as the cochlear implant 620 of FIG. 18, or a tactile output such as in the watch 320 of FIG. 13.

The processing module 30 receives sensor data 27 from the data source 20 as a time-varying dataset. The sensor data 27 may include the first data 26, the second data 28, or both. The processing module 30 may be on a smartphone, smartwatch, tablet, computer, or other static, portable or wearable device. Communication between the data source 20 and the processing module 30 may be through any wired or wireless connection. The processing module 30 may be included in a single unit with the data source 20. The data source 20 may be connected to the processing module 30 directly or through an intermediary storage and transmission device 29 for providing temporary storage of the data, depending on the particular application of the system 10.

The processing module 30 applies an adaptive localized filter process 32 to the sensor data 27 based on parameters 34, resulting in filtered data 35. The parameters 34 include an adaptive localized filter that is calculated with reference to a transform of the sensor data 27. The processing module 30 applies an event detection process 36 to the filtered data 35 to identify and characterize events, providing event data 37. The adaptive localized filter process 32 may be applied to the first sensor data 26 and the second sensor data 28 simultaneously as a combined data set, or to the first sensor data 26 and the second sensor data 28 separately.

Feedback or a summary of the events is provided to the event data module 40. The event data module 40 may include a output module 42 for communicating the event data 37 to a user or effecting a change to operation of the system 10, a storage module 44 for storing the event data 37, or both. The event data module 40 may be on a smartphone, smartwatch, tablet, computer, or other device. Communicating the event data 37 to a user may be through visualization on an optical display, vibration through a tactile display, audio communication, text message, or any suitable medium may be applied. Communication between the processing module 30 and the event data module 40 may be through any wired or wireless connection. The event data module 40 may be included in a single unit with the processing module 30.

Figure 2:
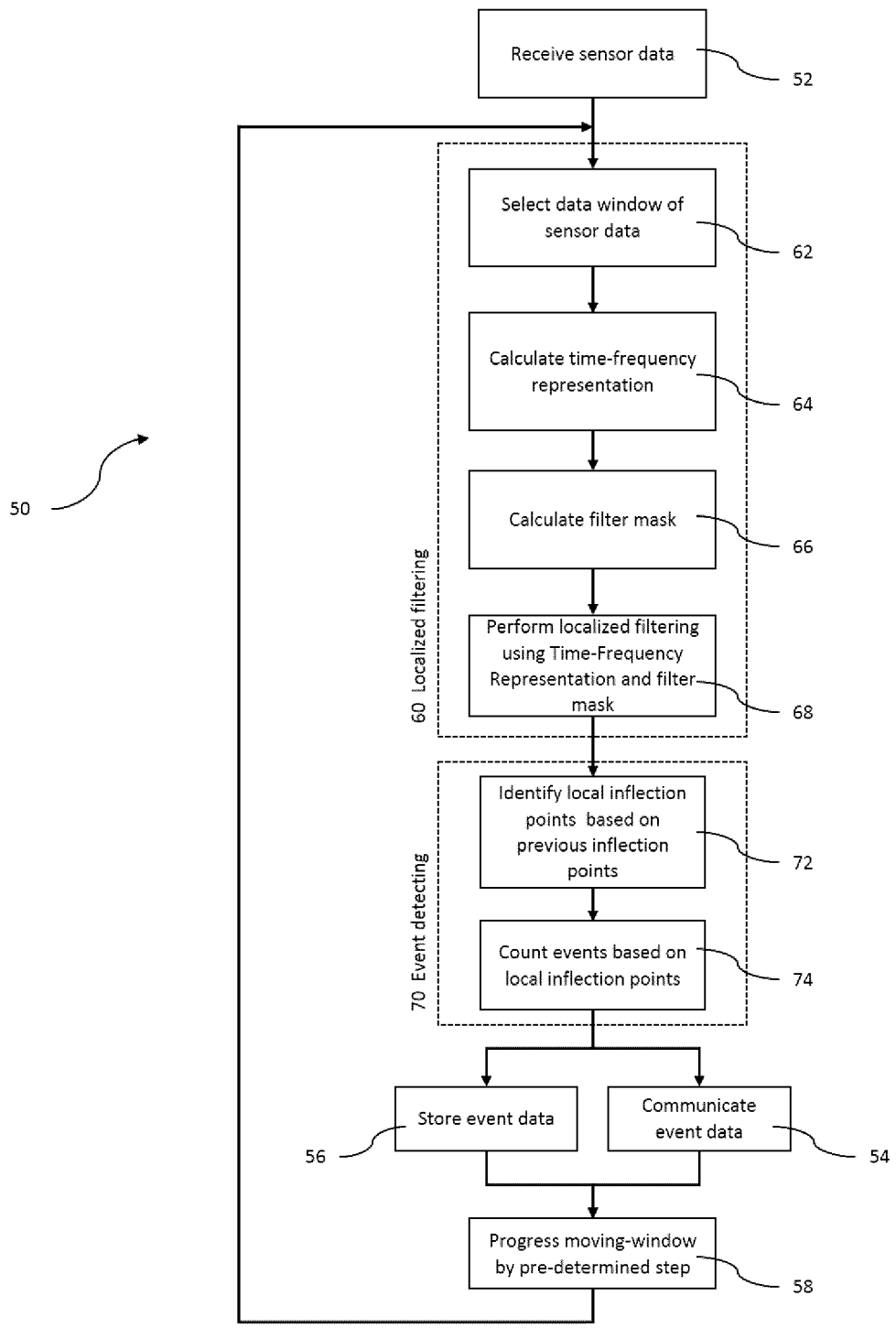
FIG. 2 is a flowchart of a method for detecting heterogeneous events.

FIG. 2 is a flowchart of a method 50 for detecting heterogeneous events. The method 50 includes a localized filtering method 60 and an event detection method 70. The method 50 includes receiving sensor data 52. Receiving sensor data 52 provides sensor data. The localized filtering method 60 is applied to the sensor data, providing filtered data. The event detection method 70 is applied to the filtered data, providing event data. Communicating the event data 54, storing the event data 56, or both, may follow applying the event detection method 70. Progressing a moving time window by a pre-determined amount of time 58 follows, and the method 50 is repeated with receiving data 52, providing additional data corresponding to the timeline defined following shifting the moving window by a pre-determined amount of time 58.

The localized filtering method 60 is applied to the sensor data. The localized filtering method 60 includes selecting a data window 62. The data window corresponds to a time period of the sensor data, which may include a plurality of data windows. Calculating a time frequency-representation 64 provides a time-frequency representation corresponding to each of the data windows. Calculating a filter mask 66 based on the time-frequency representation provides a filter mask. Localized filtering 68 is applied to the time-frequency representation using the filter mask, resulting in the filtered data. Applying each of calculating a time frequency-representation 64, calculating a filter mask 66, and localized filtering 68 to each of the plurality of data windows provides an adaptive filter for the data window to facilitate defining events in heterogeneous data.

Selecting a data window 62 may generally be referred to as a moving-window technique. Selecting a data window 62 allows the remaining steps of the localized filtering method 60 to be applied to subsequent data windows, or precedent data windows, sequentially. As a result, the localized filtering method 60 may be applied to each of the data windows as the time period of each data window passes, and it is not necessary to wait for the entire dataset to be collected before applying the filtering method 60 to any data windows that have already been selected by selecting a data window 62. Selecting a data window 62 facilitates identification of events in near real-time.

Calculating a time-frequency representation 64 on each data window facilitates calculating a filter mask 66 for each data window. Calculating a time-frequency representation 64 on each data window may be based on an S-transform, Gabor transform, or other suitable transform. The S-transform or other localizable transforms may be applied for providing localized information about the sensor data. Providing the localized transform may have advantages over a Fourier transform, which is globally-applied across a dataset as a simple frequency representation.

Calculating a filter mask 66 based on the time-frequency representation provides a filter mask. The filter mask is determined and recalculated for each data window of the time-frequency representation with reference to the characteristics of the time-frequency representation of the data window in respect of which calculating a time-frequency representation 64 is carried out.

The filter mask may remove irrelevant data and noise by applying a weighting value to each frequency for a given time point on the time-frequency representation. The filter mask may be based on the prevalence of the most and least abundant frequencies in the time-frequency representation over the time period. The filter mask may be non-binary, applying values other than 0 and 1 to each frequency in the time-frequency representation, depending on the magnitude of each frequency. In contrast, previous low-pass filters include assigning a weight of 1 to frequency values below a threshold value, and a weight of 0 to frequency values above the threshold value. Similarly, previous high-pass filters include assigning a weight of 1 to frequency values above a threshold value, and a weight of 0 to frequency values below the threshold value. In such previous approaches for detecting steps in an individual's gait, a single arbitrary threshold may be assigned without the step duration and step frequency being known. The step duration and frequency may in some cases be the information an event detection method is directed to defining, and application of a non-binary and localized filter mask may facilitate defining heterogeneous events, such as steps. An individual's gait may vary as the individual walks, runs, changes speed, climbs or descends stairs, climbs or descends a ramp or other incline, taps their feet, or makes other unpredictable actions that result in or affect an input of the sensor data.

The non-binary and adaptive features of the filter mask remove a requirement to assign a single arbitrary frequency cutoff threshold before the step duration and resulting step frequency are known. The filter mask adapts to prominent frequencies in each data window. More prominent frequency values at a given time are assigned higher weighting values, while less prominent frequencies are assigned lower weighting values. A separate filter mask is calculated for the time-frequency representation corresponding to each data window. The filter mask applied to a particular data window is the filter mask that was calculated with reference to the particular data window.

The square of the magnitude of the S-transform or other time-frequency representation at each frequency may be used as the filter mask. As a result, the more prominent frequencies in the dataset are assigned a higher mask value, and the less prominent frequencies are assigned a lower value, which may emphasize the more prominent frequencies and minimize the less prominent frequencies. Applying the square of the magnitude of the time-frequency representation may result in greater distinction between the contribution of more prominent and less prominent frequencies to the filtered data, compared with approaches in which the mask is directly proportional to the magnitude of the time-frequency representation. Where the mask may be directly proportional to the magnitude of the time-frequency representation, the difference in contribution between the more prominent and less prominent frequencies to the filtered data may be less pronounced compared with approaches in which the mask is directly proportional to the square of the magnitude of the time-frequency representation. The magnitude of the time-frequency representation and the square of the magnitude of the time-frequency representation are examples of values that may be applied. Other power relationships between the filter mask and the time-frequency representation magnitude may also be applied.

The filter mask may be non-binary and whether based on the magnitude of the time-frequency representation, the square of the magnitude of the time-frequency representation, or another power value of the magnitude of the time-frequency representation, will vary according to the abundancies of the various frequencies of each time point in the data window in respect of which the time-frequency representation and the relevant filter masks are calculated.

Localized filtering 68 is applied to the time-frequency representation using the filter mask, resulting in the filtered data. The localized filtering 68 may include multiplication of the filter equation with the time-frequency representation of the data window and converting the time-frequency representation back into the time-domain. The time-frequency representation may be converted back into the time-domain by an inverse S-transform, an inverse Gabor transform, or any suitable transform. The filtered data may then be further processed in the time domain, such as by the event detection method 70. The inverse transform may be completed by any suitable approach . . . may be completed by any suitable approach, such as the time inverse transform described in M. Schimmel, J. Gallart, "The inverse S-transform in filters with time-frequency localization", IEEE Transactions on Signal Processing, Vol. 53, No. 11, 4417-4422, 2005.

Where the magnitudes of the time-frequency representation are large, or result in large deviations between the resulting magnitudes of the time-frequency representation at more prominent frequencies compared with less prominent frequencies at a given time point in the time period, there may be advantages to normalizing the values against the greatest magnitude in the filtered data, after squaring or applying other power relationships to the magnitudes of the time-frequency representation. Such a normalization would result in each data point in the filtered data having a value varying between 0 and 1. The normalized values may result in a more recognizable plot of events for visualization by a user than would be the case where the localized filtering 68 is applied to the time-frequency transform values without normalization. However, the event detection method 70 may be applied to the filtered data regardless of whether the magnitudes of the time-frequency transform values (or the magnitudes elevated to a power) are normalized before localized filtering 68 is applied to the magnitudes of the time-frequency transform.

The event detection method 70 is applied to the filtered data. The event detection method 70 includes identifying features 72 and counting events based on the features 74.

Identifying features 72 may be based on the event duration being greater than a defined minimum event duration, less than a defined maximum duration, or both. Identifying features 72 may be based on the event magnitude being greater than a defined minimum event magnitude, less than a defined maximum event magnitude, or both. Inflection points, such as local minima, local maxima, or both may be used to detect the beginnings and ends of events.

Counting events based on features 74 may be applied to each data window based on the criteria used for identifying features 72 based on previous inflection points. Depending on the difference in the magnitude of, or time elapsed between, local extrema, other inflection points or other features, some features may be determined to define endpoints of constituent events within an overall aggregated event including the constituent events, when counting events based on features 74.

After the events are counted within a given data window, the method 50 may include communicating the event data to a user 54, storing the event data 56, or both. After communicating the event data 54, storing the event data 56, or both, progressing a moving time window by a pre-determined amount of time 58 may precede receiving sensor data 52 in a application of the method 50 to a subsequent data window. The corresponding sensor data for a subsequent data window is received and the localized filtering method 60 and the event detection method 70 are applied to the subsequent data window.

Communicating the event data 54 may include communicating in real time with a user who is applying the method 50. Communicating the event data 54 may involve a prompt to encourage a habit that is expected to improve performance, avoid injury or otherwise provide a benefit. Communicating the event data 54 may also be to a person who is not the source of the stimulus the leads to receiving sensor data 52.

Storing the event data 56 may include storing details of features and events defined by the event data. Following filtering and transformation back into the time domain, the previously recorded inflection points may be used as a reference point for defining events. The type of extrema to search for may be selected based on the previous data window. Where the previous data window included a maximum as an inflection point, then a minimum in the following data window may be the search target. Where the previous data window included a minimum as an inflection point, then a maximum in the following data window may be the search target.

Figure 3:
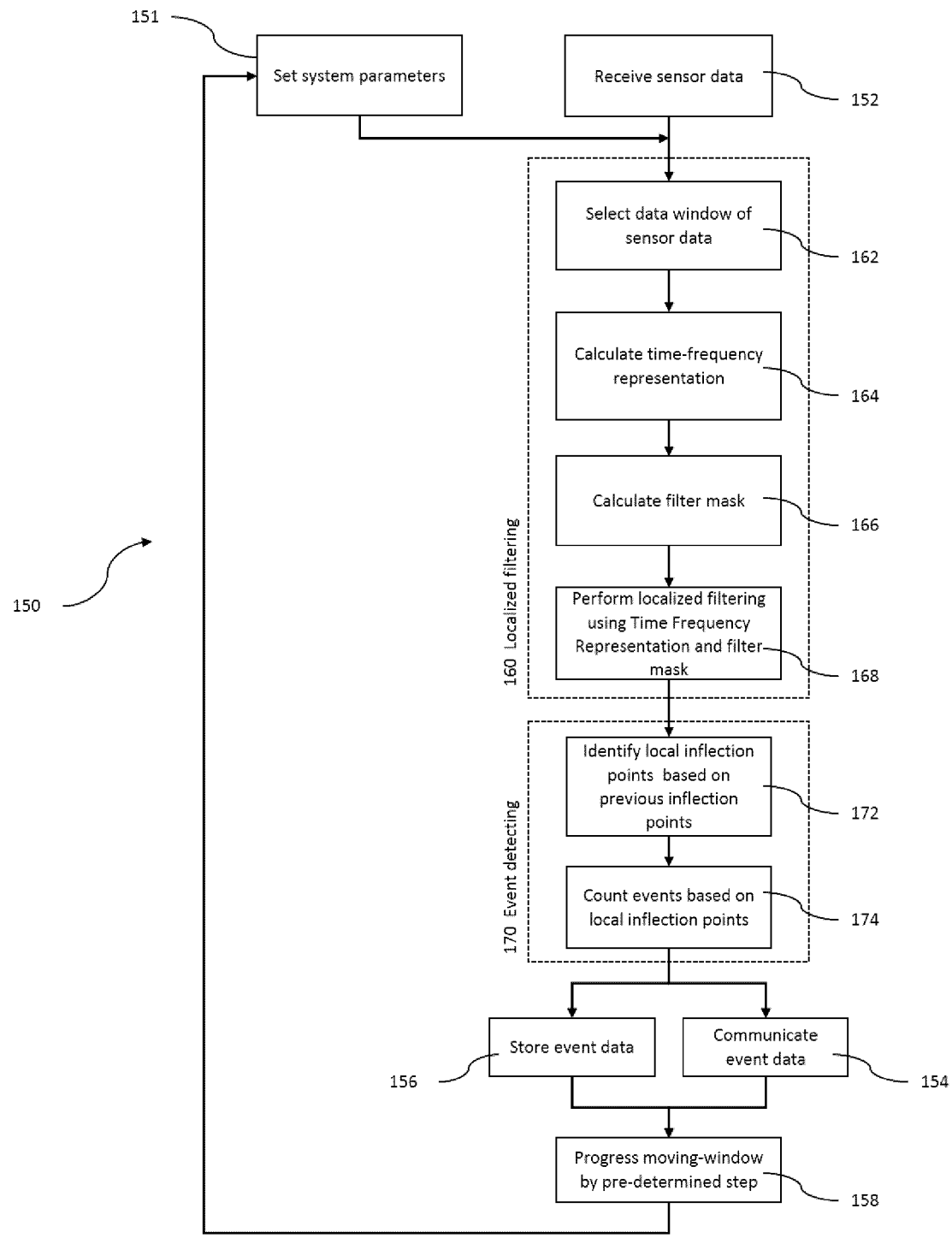
FIG. 3 is a flowchart of a method for detecting heterogeneous events

FIG. 3 is a flowchart of a method 150 for detecting heterogeneous events. The method 150 includes the localized filtering method 160 and the event detection method 170. The method 150 includes defining parameters 151. In some applications, the parameters may already be set or may not be definable by a user or otherwise, and defining parameters 151 may be absent from a method for detecting heterogeneous events (e.g. the method 50, etc.). The method 150 includes receiving sensor data 152, resulting in the sensor data. The localized filtering method 160 is applied to the sensor data, resulting in the filtered data. The event detection method 170 is applied to the filtered data, resulting in the event data. Communicating the event data 154, storing the event data 156, or both, may follow applying the event detection method 170. Progressing a moving time window by a pre-determined amount of time 158 follows, and the method 150 is repeated with receiving data 152, providing additional data corresponding to the timeline defined following shifting the moving window by a pre-determined amount of time 158.

The localized filtering method 160 is applied to the sensor data. The localized filtering method 160 includes selecting a data window 162. The data window corresponds to a time period of the sensor data, which may include a plurality of data windows. Calculating a time frequency-representation 164 provides a time-frequency representation corresponding to each of the data windows. Calculating a filter mask 166 based on the time-frequency representation provides a filter mask. Localized filtering 168 is applied to the time-frequency representation using the filter mask, resulting in the filtered data. Applying each of calculating a time frequency-representation 164, calculating a filter mask 166, and localized filtering 168 to each of the plurality of data windows provides an adaptive filter for the data window, to facilitate defining events in heterogeneous data.

Defining parameters 151 may take place for each data window. Defining parameters 151 may include defining upstream parameters such as the time scale of each data window, or any details of calculating the time-frequency representation 164, calculating the filter mask 166, or performing localized filtering 168. The time scale may be selected with reference to the type of events that are expected. In applications where receiving sensor data 152 is directed to sensor data of an individual's gait, a normal step may take between 0.5 and 2 seconds. The minimum and maximum window time scales may be placed around this estimated duration accordingly, such that much shorter or much longer steps would not be considered. The minimum step time scale may be related to the time scale of the previous step. An individual step may be defined as longer than 25% of the duration of the previous step, otherwise it will be treated as part of the previous step. Similarly, an individual step may be defined with reference to the force of a footfall on the previous step and any relationship from a baseline force, to distinguish sensor data of the individual taking distinct steps from sensor data of the individual shifting their weight without taking a step. Defining individual steps with reference to magnitude of footfall force may also facilitate defining jump landings, steps on stairs, steps on ramps, steps after taking on a significant load, or other heterogeneous events that are indicative of different types of steps or other activities that register force on a footfall.

Defining parameters 151 may also include updating downstream user-experience functions of the system within which the method 150 is practiced. In applications that use an insole or other plantar pressure sensors, this may include inflating or deflating bladders around an insole, changing stiffness of wrist or other joint braces, changing output from a hearing aid, changing the pace of a metronome, or other functions.

The method 50 and the method 150 may each be carried out with the system 10. The sensor data 27 may be received by the processing module 30 from the data source 20 at a predetermined frequency, in some cases via temporary storage 29. The localized filter process 32 may be applied to the sensor data 27 to apply the localized filtering method 60. The event detection process 36 may be applied to the filtered data 35 to carry out the event detection method 70. The event data 37 may be applied in communicating the event data 54 to the user through the output module 42, in storing the event data 56 in the storage module 44, or both. The sensor data 27 may generally be represented as a time-varying signal. Where the sensor data 27 includes pressure data, the pressure data may represent the application of pressure over a defined amount of time.

The rate at which the sensor data 27 is sampled from the data source 20 may be adjusted according to the data set after the localized filtering method 60 has been applied to sensor data 27. Some applications may benefit from greater resolution in the sensor data 27 while other applications may benefit from down-sampling to conserve bandwidth in the sensor data 27 or increase event detection speed.

FIGS. 4A to 7C show simulated sensor data, time-frequency representations, and filtered data in a test application of the method 50 to simulated pressure sensor data that would be obtained in a system similar to the system 10 adapted for use on feet, similarly to the system 210 of FIG. 8 or the system 310 of FIG. 13.

The simulated sensor data was modified from empirical pressure data acquired with a single pressure sensor. The simulated sensor data was modified to increase heterogeneity of events to be characterized by application of the method 50. The individual events represented in the simulated sensor data differ in their specific pressure-time profiles more than individual events tend to from empirical pressure data. The simulated sensor data corresponded to sensor data from a pressure sensor of the types of events that may be seen when applying the method and system to an individual who is walking to measure steps or other events related to the individual's gait (e.g. changing speed, climbing stairs, walking on a ramp or other incline, tapping feet, etc.).

Two low-pass Fourier transforms were applied to the simulated sensor data, in each case resulting in a frequency representation. The two low-pass Fourier transforms used two different cut-off frequencies.

Two S-transforms were applied to the simulated sensor data, in each case resulting in a time-frequency representation. A first adaptive localized filter was based on the magnitude of an S-transform of the simulated sensor data. A second adaptive localized filter was based on the square of the magnitude of the S-transform of the simulated sensor data.

Normalization was not applied to the filtered data. As further described below with reference to FIGS. 4A to 7C, the adaptive filter provides more accurate event detection than the filter based on a Fourier transform. In one case, a previous filter based on low-pass Fourier transform identified two events as one, while the adaptive filter correctly identified the two separate events.

Figure 4A:
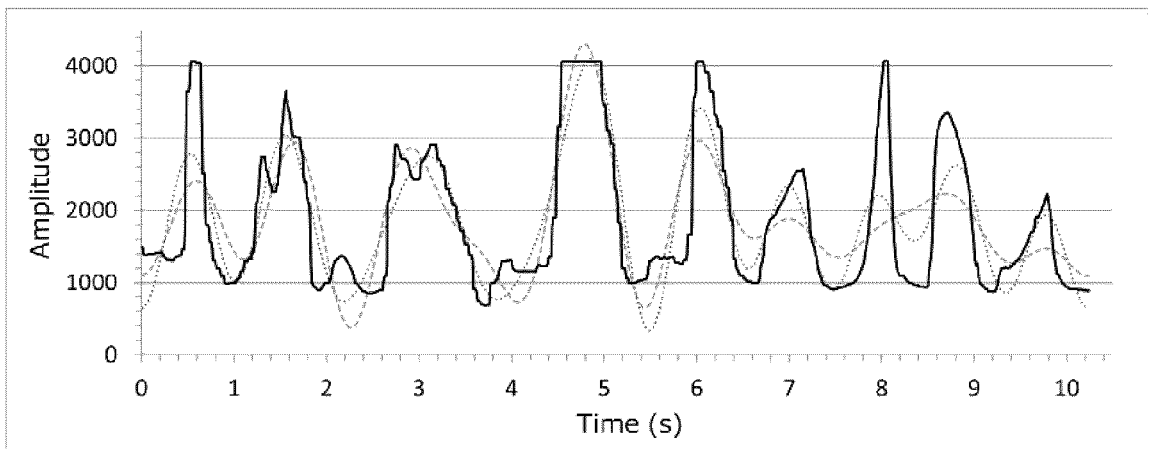
FIG. 4A is an example pressure data series filtered with two Fourier transforms at two cut-off frequencies.
Figure 4B:
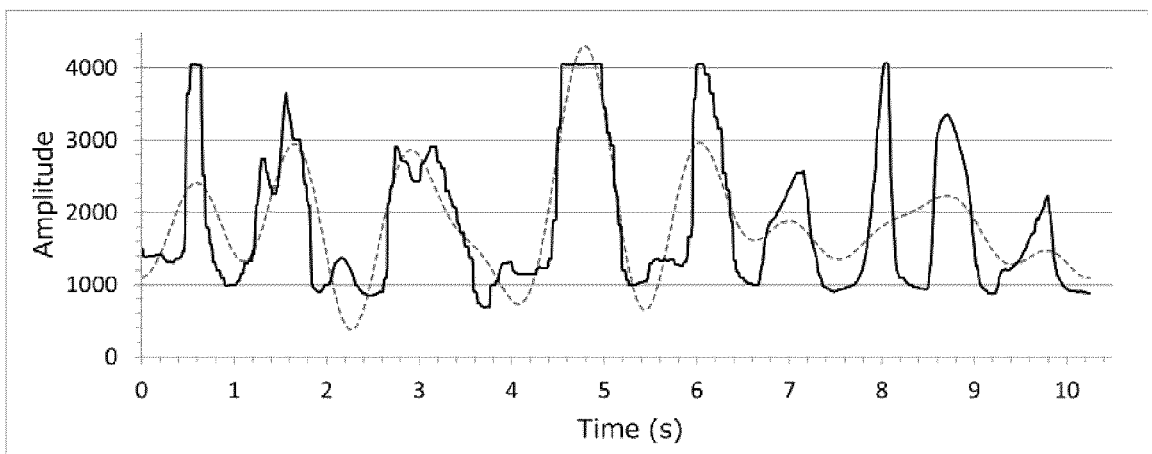
FIG. 4B is the data series of FIG. 4A showing only one of the Fourier transforms and the sensor data.
Figure 4C:
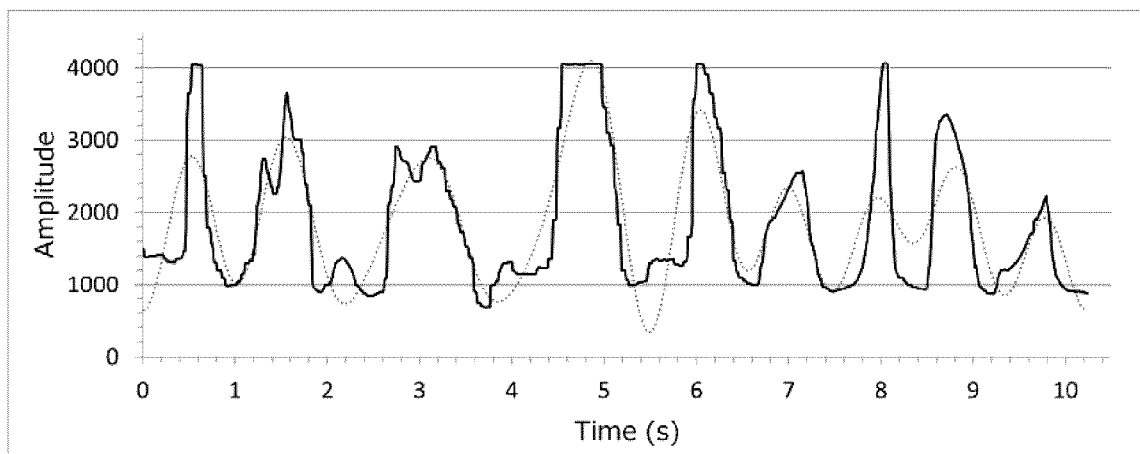
FIG. 4C is the data series of FIG. 4A showing only one of the Fourier transforms and the sensor data.

FIGS. 4A, 4B, and 4C show the simulated sensor data series (solid lines) as received from sensors, and filtered data obtained using a low-pass Fourier transform approach, which applies to the entire data set, as opposed to the localized and adaptive approach of the method 50. FIG. 4A shows filtered data obtained by applying a low-pass Fourier transform-based filter with a first cut-off frequency to the simulated sensor data (dashed lines). FIG. 4A shows filtered data obtained by applying a low-pass Fourier transform filter with a second cut-off frequency to the simulated sensor data (dotted lines). FIG. 4B shows only the simulated sensor data (solid lines) and the filtered data at the first cut-off frequency (dashed lines). FIG. 4C shows only the simulated sensor data (solid lines) and the filtered data at the second cut-off frequency (dotted lines).

The first cut-off frequency is lower than the second cut-off frequency. As can be seen at between about 750 and about 950 seconds, two peaks in the simulated sensor data were interpreted as one event in the filtered data at the first cut-off frequency (dashed lines).

Figure 5:
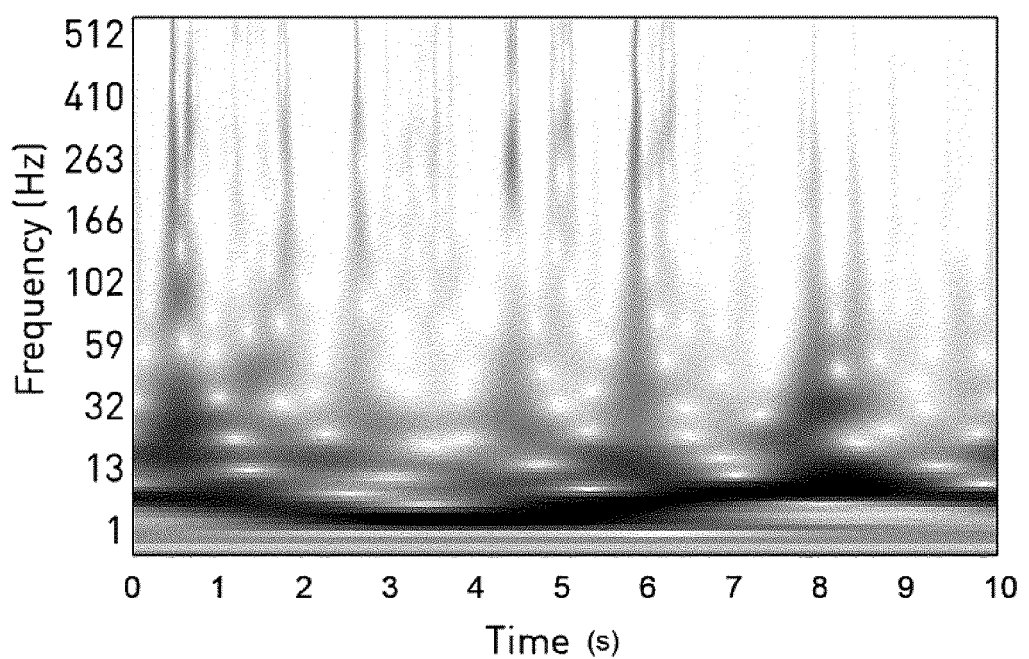
FIG. 5 is an S-transform time-frequency plot of the data series of FIG. 4A.

FIG. 5 is a time-frequency representation plot of the same simulated sensor data of FIG. 4A after a localized S-transform of the simulated sensor data, as in the calculating a time frequency-representation 64 portion of the method 50. A filter mask is determined for each data window of the sensor data with reference to the time-frequency plot of FIG. 5 corresponding to the respective time period as in the method 50 in the calculating a filter mask 66 portion of the localized filtering method 60. The respective filter masks are applied to the time-frequency representation of FIG. 5 when filtering the data during localized filtering 68 in the method 50. The filter mask for each data window in time is determined with reference to the magnitudes of each frequency at the data window of the time-frequency representation.

Figure 6A:
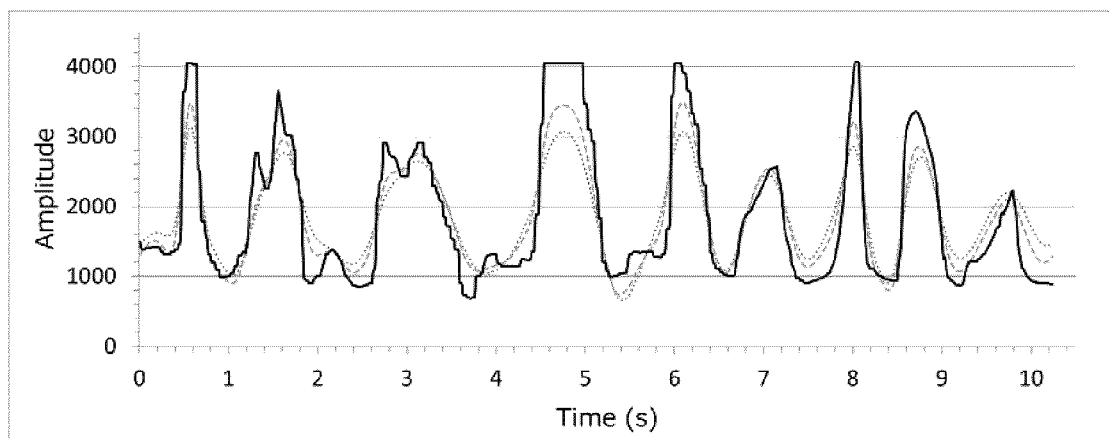
FIG. 6A is the data series of FIG. 3 filtered with two adaptive, localized filters, one based on the magnitude of the S-transform shown in FIG. 5 and another based on the square of the magnitude of the S-transform shown in FIG. 5.
Figure 6B:
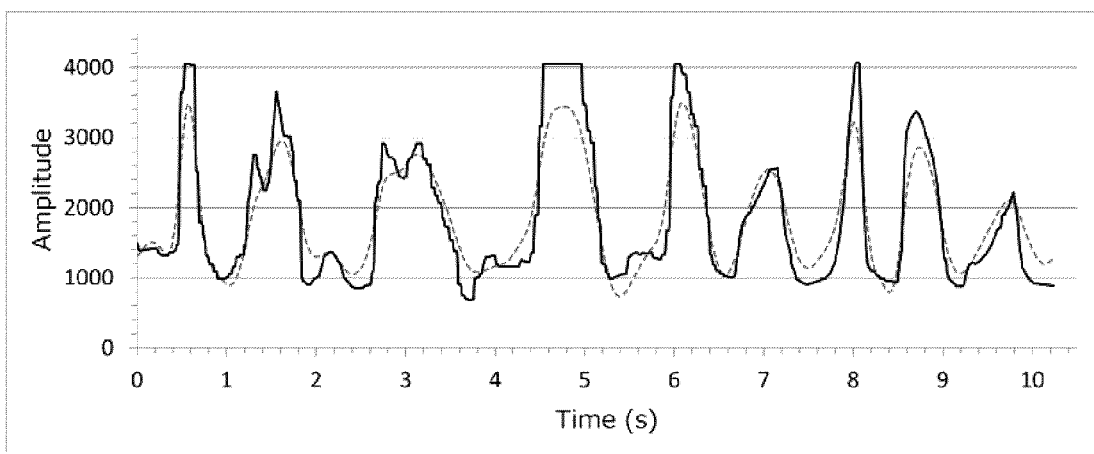
FIG. 6B is the data series of FIG. 6A showing only the filter based on the magnitude of the S-transform shown in FIG. 5 and the sensor data.
Figure 6C:
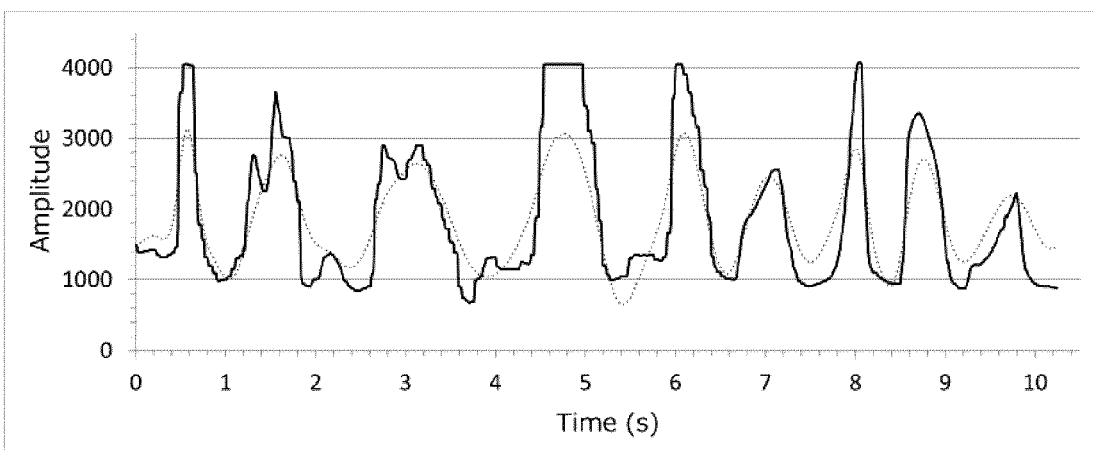
FIG. 6C is the data series of FIG. 6A showing only the filter based on the square of the magnitude of the S-transform shown in FIG. 5 and the sensor data.

FIGS. 6A, 6B, and 6C show the simulated sensor data of FIG. 4A (solid line in each of FIGS. 6A, 6B, and 6C) and resulting filtered signal using an adaptive, localized filtering method include features from the method 50 as shown in FIG. 2. FIG. 6A also shows filtered data obtained by applying a filter mask proportional to the time-frequency representation magnitude (dashed lines). FIG. 6A also shows filtered data obtained by applying a filter mask proportional to the square of the time-frequency transformation (dotted lines). FIG. 6B shows only the simulated sensor data (solid lines) and the filtered data based on the magnitude of the time-frequency representation (dashed lines). FIG. 6C shows only the simulated sensor data (solid lines) and the filtered data based on the square of the magnitude of the time-frequency representation (dotted lines).

Figure 6D:
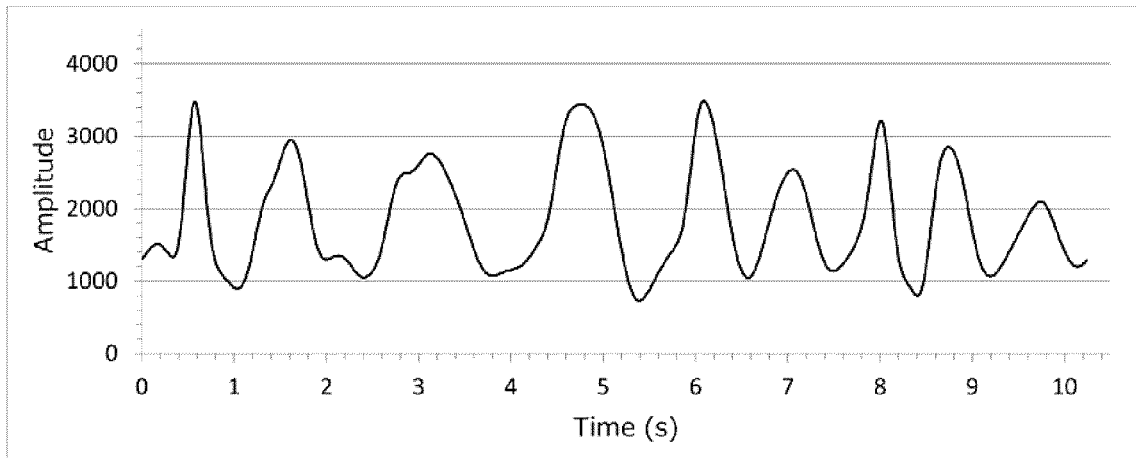
FIG. 6D is the data series of FIG. 6A showing only the filter based on the magnitude of the S-transform shown in FIG. 5.
Figure 6E:
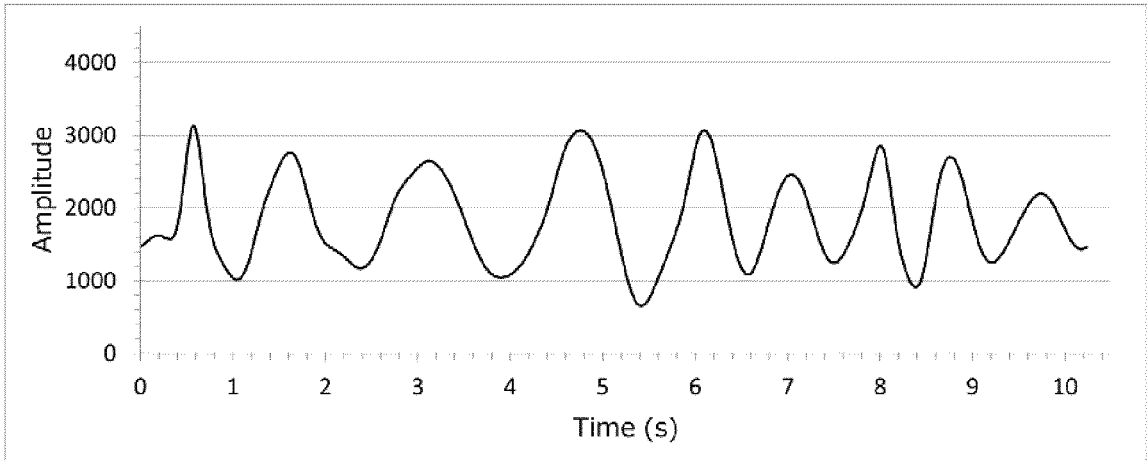
FIG. 6E is the data series of FIG. 6A showing only the filter based on the square of the magnitude of the S-transform shown in FIG. 5.

FIG. 6D shows only the filtered data based on the magnitude of the time-frequency representation (solid lines). FIG. 6E shows only the filtered data based on the square of the magnitude of the time-frequency representation (solid lines).

As can be seen at between about 750 and about 950 seconds, the two peaks in the simulated sensor data that were interpreted as one event in the filtered data at the first cut-off frequency of the Fourier transform (dashed lines in FIGS. 4A and 4B) were interpreted as separate events when applying the adaptive localized filter based on the localized time-frequency representations.

Figure 7A:
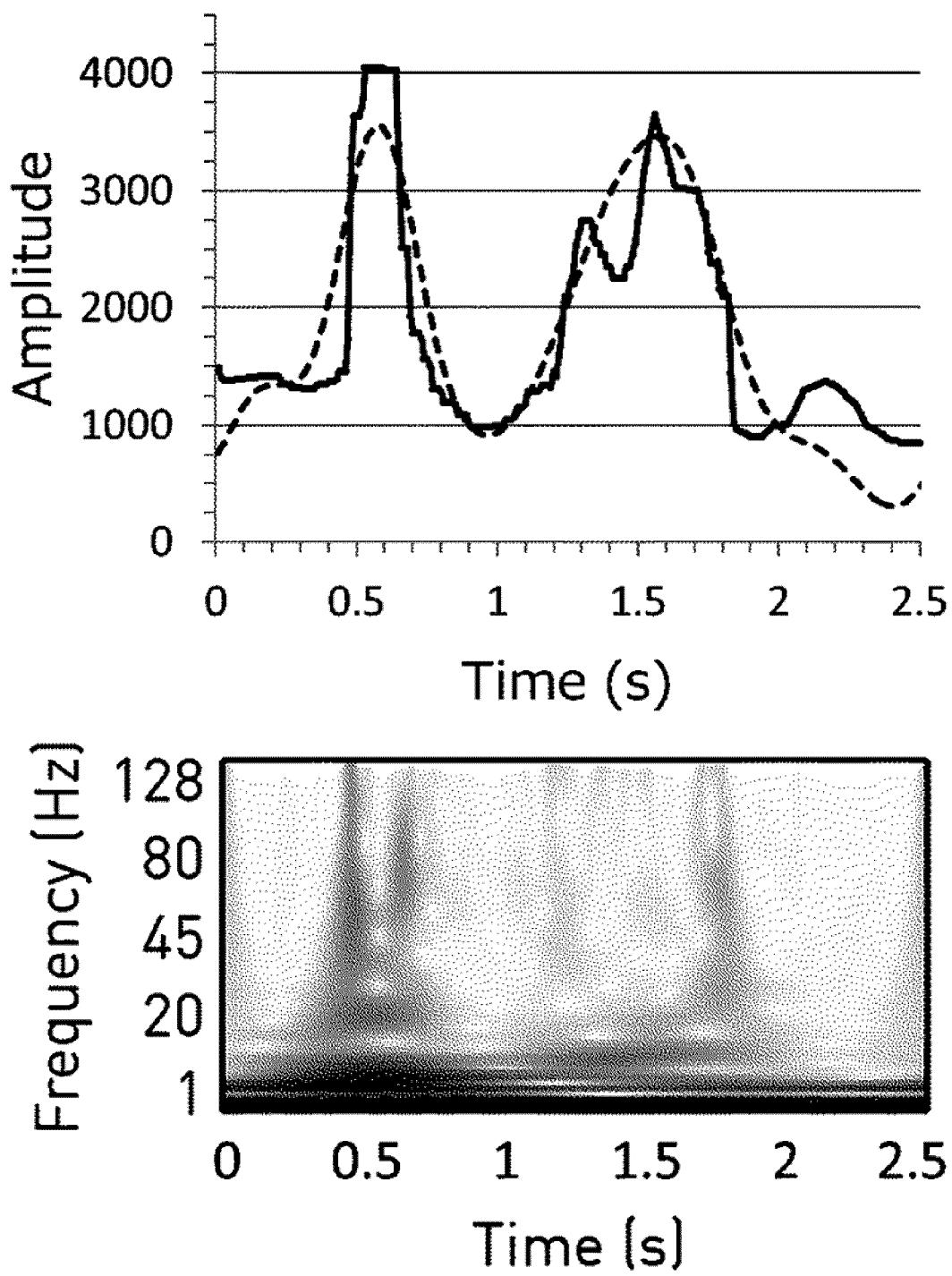
FIG. 7A shows S-transform magnitudes and corresponding signals filtered with adaptive localized filtering based on the magnitude of the S-transform, from 0 to 250 seconds of the data shown in FIGS. 4A to 6E.
Figure 7B:
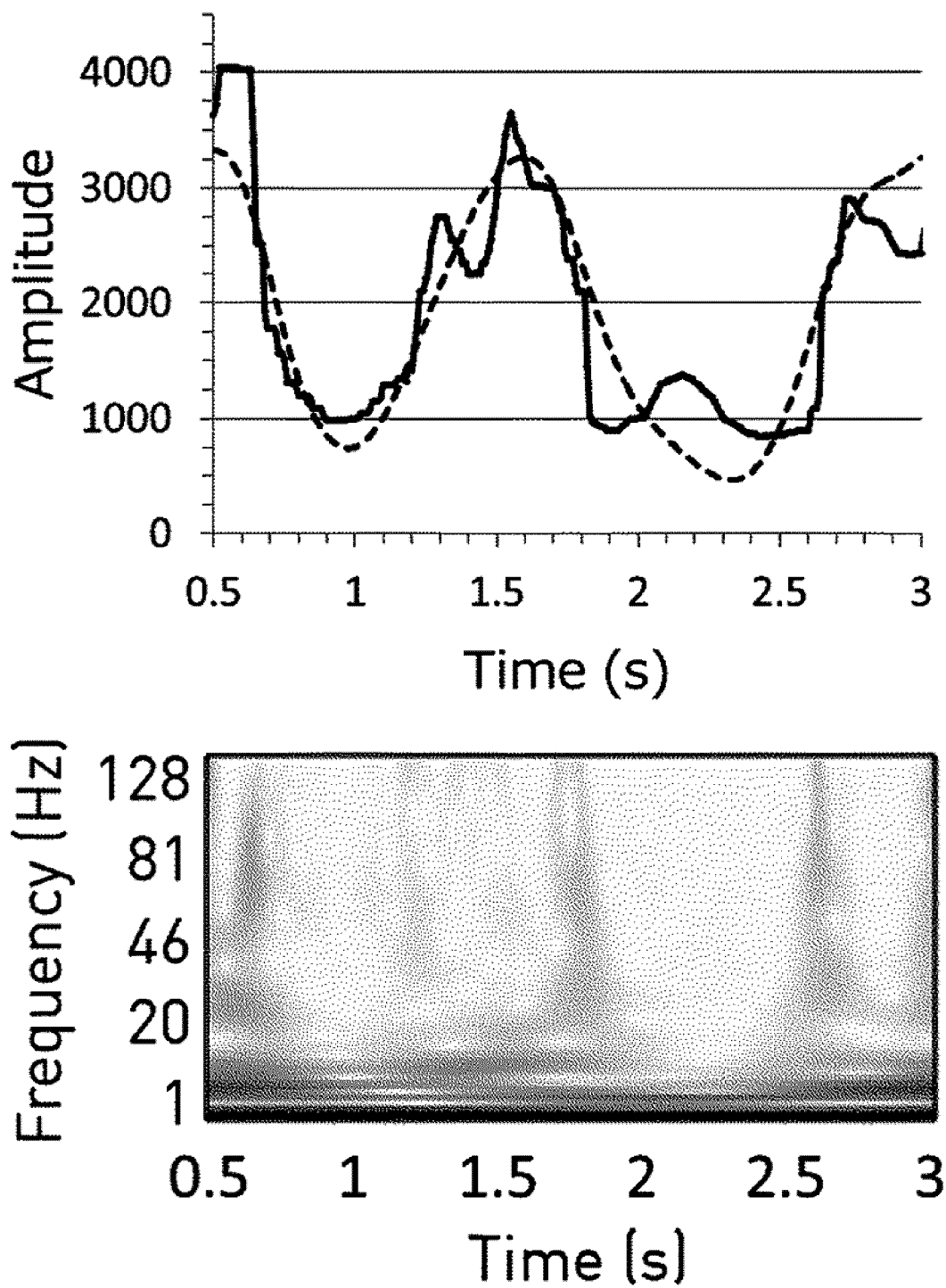
FIG. 7B shows S-transform magnitudes and corresponding signals filtered with adaptive localized filtering based on the magnitude of the S-transform, from 50 to 300 seconds of the data shown in FIGS. 4A to 6E.
Figure 7C:
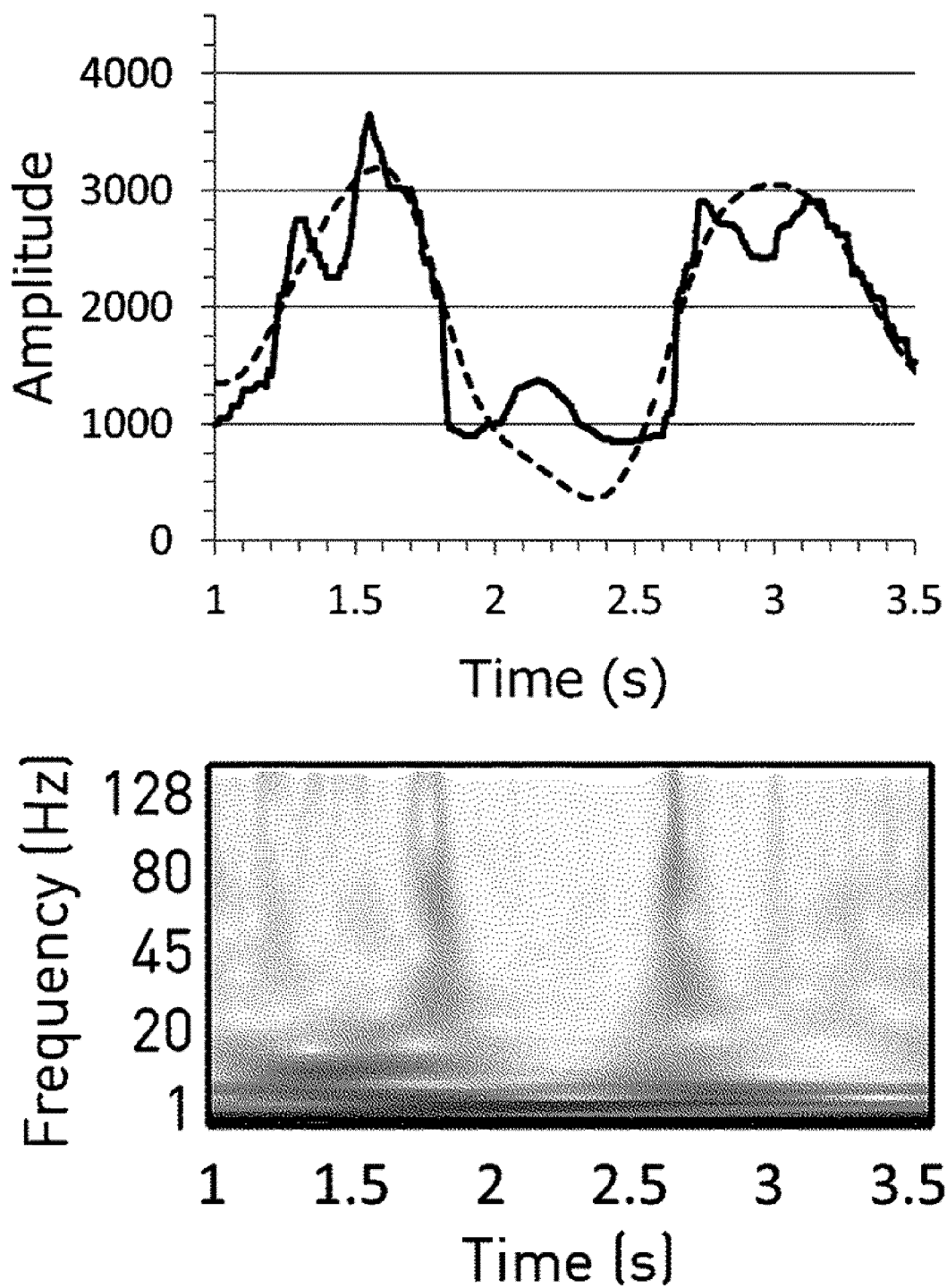
FIG. 7C shows S-transform magnitudes and corresponding signals filtered with adaptive localized filtering based on the magnitude of the S-transform, from 100 to 350 seconds of the data shown in FIGS. 4A to 6E.

FIGS. 7A, 7B, and 7C show a series of time-frequency representation magnitude plots of the simulated sensor data after a localized S-transform of the simulated sensor data (bottom). FIGS. 7A, 7B, and 7C also show plots (top) of corresponding sensor data (solid lines), filtered signal using an adaptive localized filtering technique in the current data window based on the square of the magnitude of the time-frequency representation (dashed lines; the same plots shown in FIGS. 6A, 6C, and 6E). FIG. 7A shows sensor data and filtered data from 0 to 250 seconds, FIG. 7B shows sensor data and filtered data from 50 to 300 seconds, and FIG. 7C shows sensor data and filtered data from 100 to 350 seconds.

This example application shows source data filtered in accordance with the localized filtering method 60 in FIGS. 6A, 6B, and 6C. In contrast, FIGS. 4A, 4B, and 4C shows application of a Fourier transform to the global dataset. As shown in FIGS. 7A, 7B, and 7C, the localized filtering method 60 provides a filtered time-representation of the pressure data that highlights the most prominent events or steps, and minimizes the noisy, least important components of the signal.

As shown by comparing the plots of the filtered data obtained by filtering the source data using the global filter (FIGS. 4A to 4C) with plots of the filtered data obtained by filtering the source data using the adaptive localized filter (FIGS. 6A to 6E), the adaptive localized filter provides filtered data more closely approximating the simulated sensor data in several portions of the pressure-time curve. Several specific examples of the adaptive filter more closely approximating the simulated sensor data follow below.

The peak at about 50 seconds is more closely approximated by the adaptive localized filter.

When detecting events that are steps taken by an individual, a hard "heel first" strike, followed by contact at the ball of the foot may result in the double peak in the simulated sensor data as shown around 150 seconds in FIGS. 6A to 6E. The adaptive localized filter correctly interpreted this event as a single step. While the global Fourier transform filters applied in FIGS. 4A to 4C also defined the step around 150 seconds as a single step, in other cases a simple high-pass or low-pass filter may not provide the same accuracy. The troughs at about 225 seconds are deeper and further from the simulated sensor data in the global Fourier transform filter compared with the adaptive localized filter.

Between about 600 and about 1000 seconds, the adaptive localized filter more closely follows the simulated sensor data contours than the global Fourier transform filter. As can be seen at between about 750 and about 950 seconds, two peaks in the simulated sensor data were interpreted as one event in the filtered data at the first cut-off frequency (dashed lines).

Each of the adaptive localized filters applied show nine events, as most simply shown in FIGS. 6D and 6E. The nine events would be counted by application of the event detection method 70. In contrast, the global Fourier transform with the first (lower) cut-off frequency misinterpreted two events as one between about 750 and about 950 seconds. The increased accuracy in characterizing heterogeneous events may be facilitated by application of adaptive localized filtering based on the magnitude (or the magnitude elevated to a power) of a localized time-frequency representation determined within a progressing window of the simulated sensor data.

The simulated sensor data show a well-defined baseline, which facilitates application of the global Fourier transform. In other applications with a drifting baseline, the global Fourier transform may be more likely to result in inaccurate filtering of the time-frequency representation and inaccurate event detection. Similarly, the adaptive localized filtering method may provide additional advantages for applications with a drifting baseline.

FIG. 8 shows a schematic of an event detection system 210. The data source 220 includes the first pressure sensor 222 and the second pressure sensor 224 on a footwear insert for a subject individual's foot. In such applications, the first pressure sensor 222 may be located at a location corresponding to a heel of a foot on the data source 220. The second pressure sensor 224 may be located at a location corresponding to a ball of a foot on the data source 220. Sensor data 227 collected by the pressure sensor system 220 may then be transmitted by an intermediary storage and transmission device 229, and analyzed by the processing module 230 inside a laptop computer. The laptop computer also includes an event data module 240. The event data module 240 communicate the event data 237 to the communication module 242, stored by a storage module 244, or both.

Figure 9:
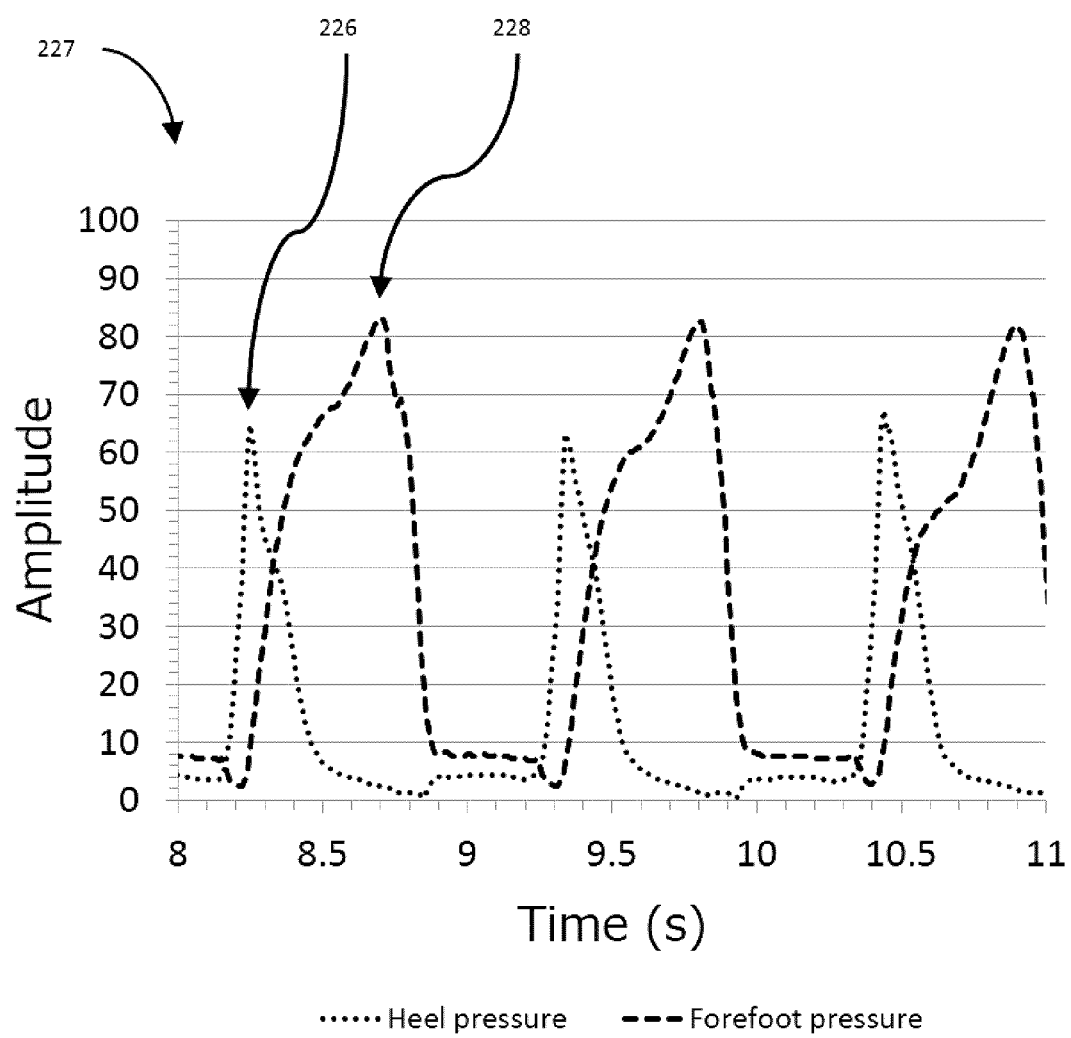
FIG. 9 is a plot of idealized sensor data of the event detection system of FIG. 8.

FIG. 9 is a plot of idealized sensor data 227 obtained with the event detection system 210. The first sensor data 226 (dotted lines) from the first sensor 222 at the heel of a foot, and the second sensor data 228 (dashed lines) from the second sensor 224 at the forefoot, also called the ball of the foot, where the metatarsals are located, are both shown on the plot. The sensor data 227 may be obtained by applying the method 50 or the method 150 using the system 220.

Figure 10:
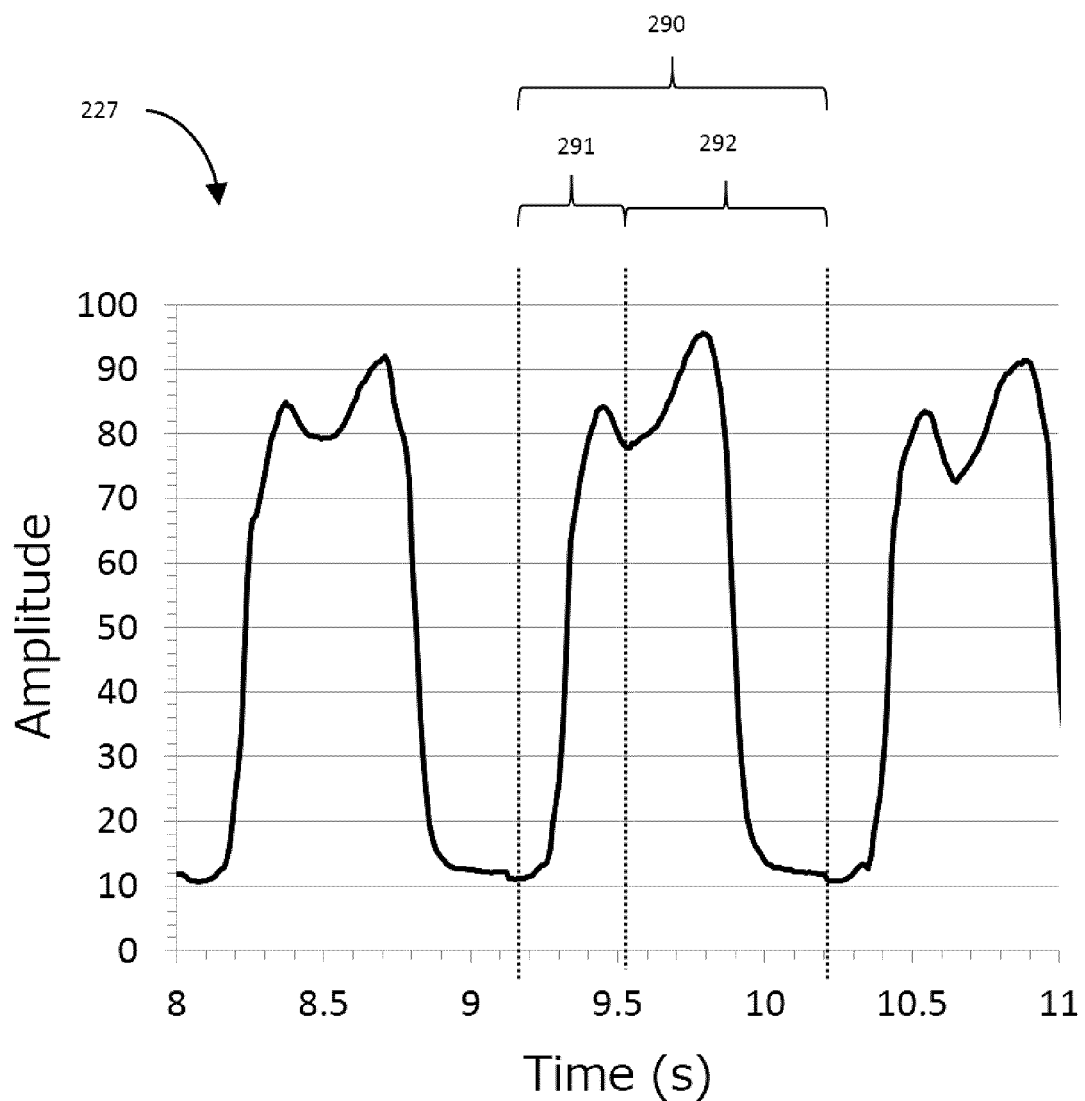
FIG. 10 is a plot of summation data based on the sensor data of FIG. 9.

FIG. 10 is a plot of summation data based on the sensor data 227 of FIG. 9 showing the idealized sensor data 227 as a summation of the first sensor data 226 and second sensor data 228. Within the sensor data 227, various events may be identified, characterized and bound by points of inflection within the sensor data 227. An entire step event 290 may be considered an event, which is bound in the time dimensions by inflection points that deviate from the baseline reading. However, smaller component events of the step event 290 include a heel strike 291 that may be recorded by the first pressure sensor 222 at the heel, and a forefoot strike 292 that may be recorded by the second pressure sensor 224 at the forefoot. Both heel strike 291 and forefoot strike 292 are defined by apparent inflection points within the sensor data 227, which has a drifting base line.

Figure 11A:
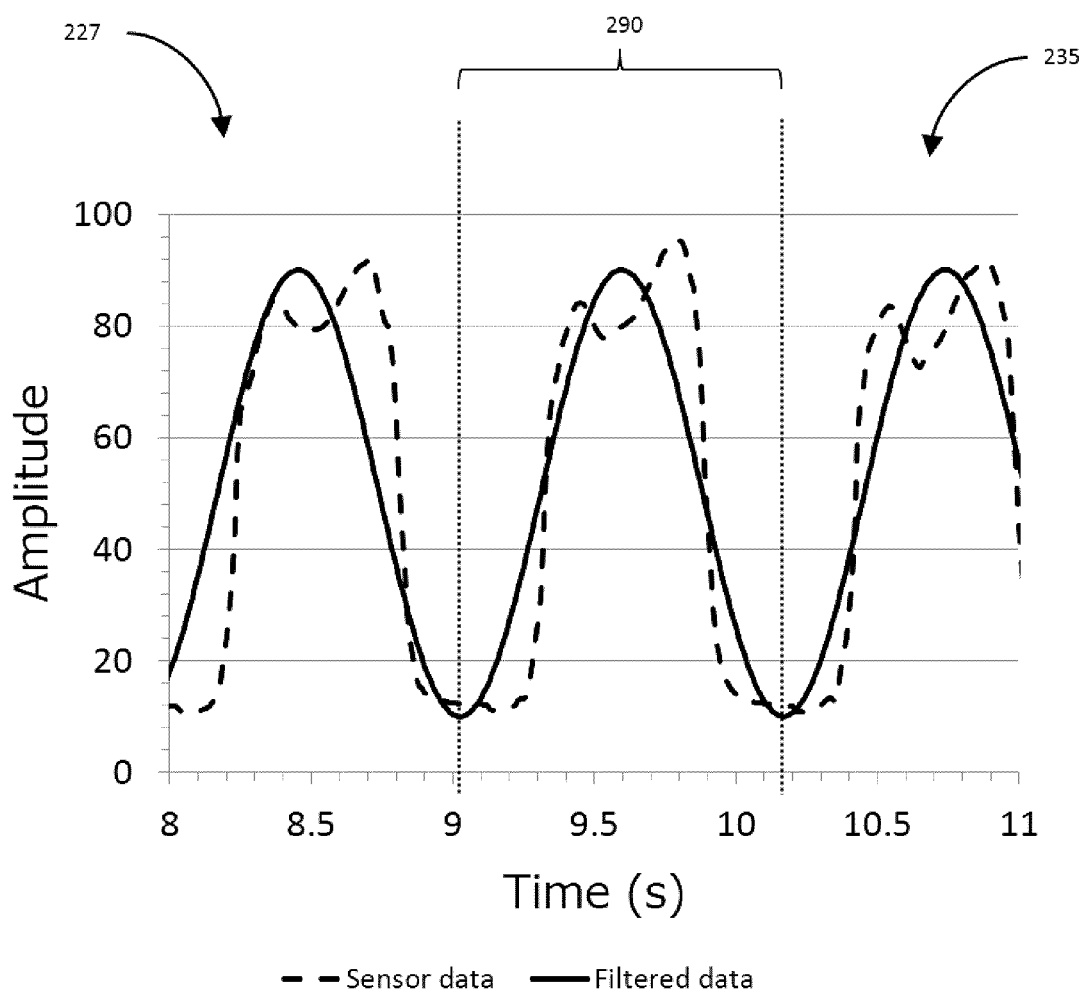
FIGS. 11*a* to 11*f* are a plots of filtered data based on the sensor data of FIG. 9 and the sensor data of FIG. 9.

FIG. 11a is a plot of filtered data 235 (solid lines) based on the sensor data 227 of FIG. 9 (dashed lines). The step event 290 is shown in the filtered data as a single event without the first event 291 and the second event 292. Using the filtered data, the bounds of the step event 290 can be identified with greater accuracy than the step event 290 was identified in FIG. 10 based on the sensor data. The drifting baseline is filtered out of the sensor data 227. In this example, the encompassing event is an entire step event 290, defined by the inflection points of the filtered data 235, in this case, minima in the filtered data 235 that correspond to non-extrema inflection points in the sensor data 227.

Figure 11B:
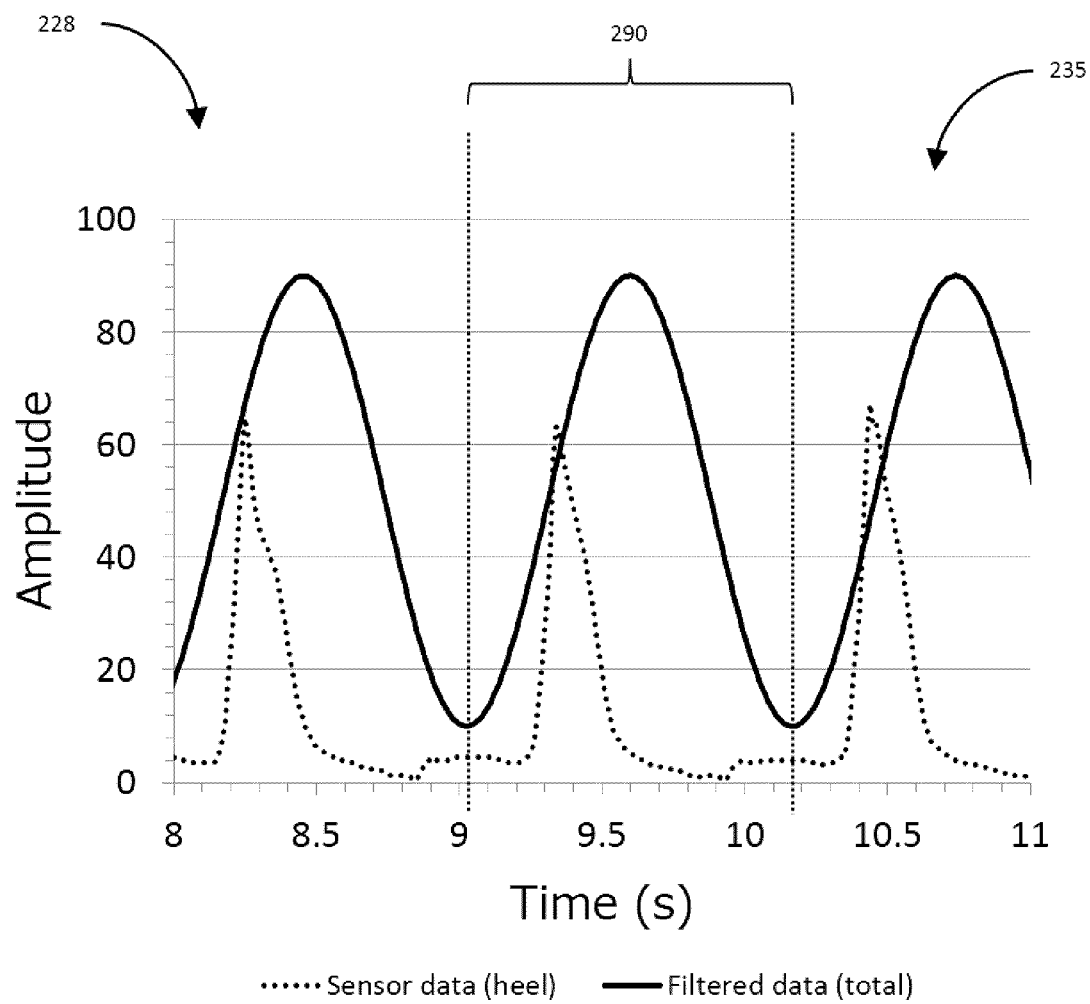
Figure 11C:
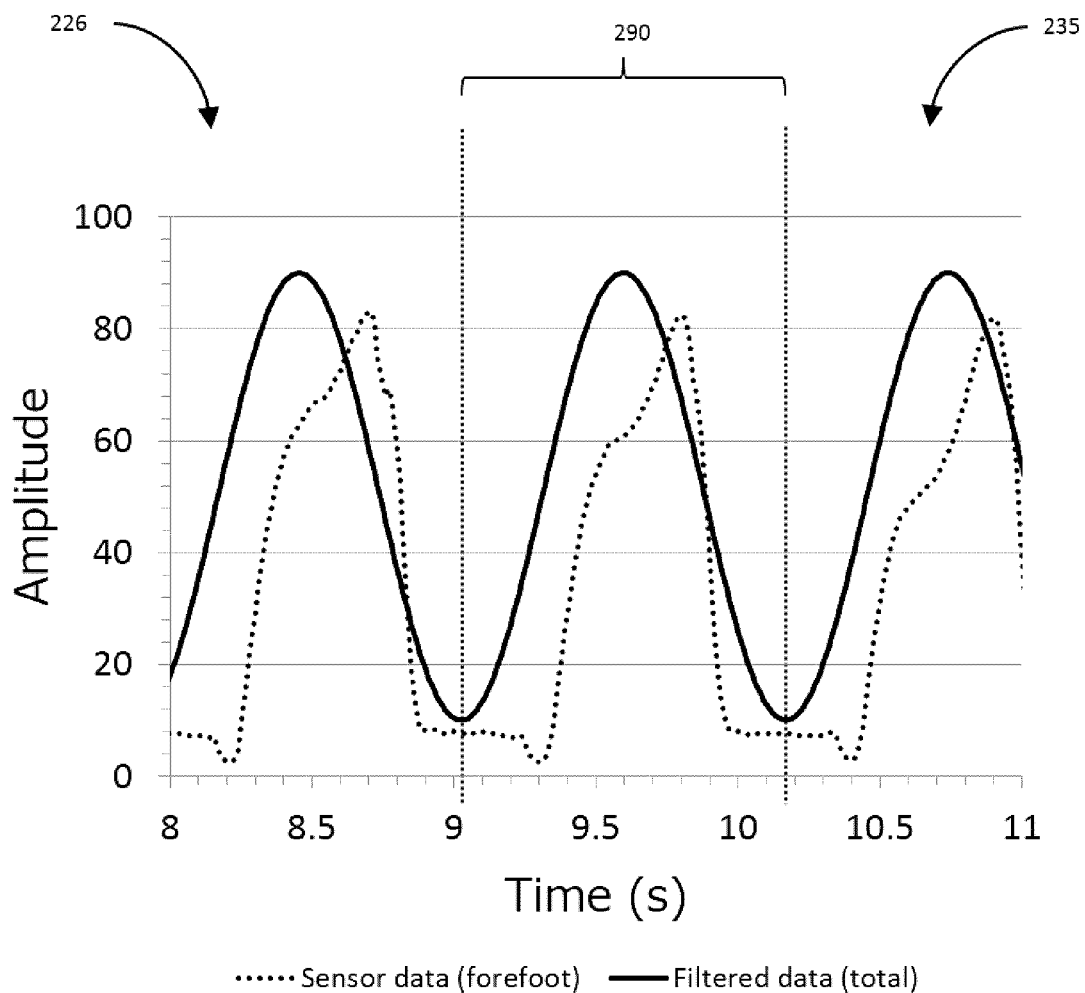

FIGS. 11b and 11c show the sensor data 227 from the heel (dashed lines in 11b) and the forefoot (dashed lines in 11c) superimposed over the filtered data 235.

Figure 11D:
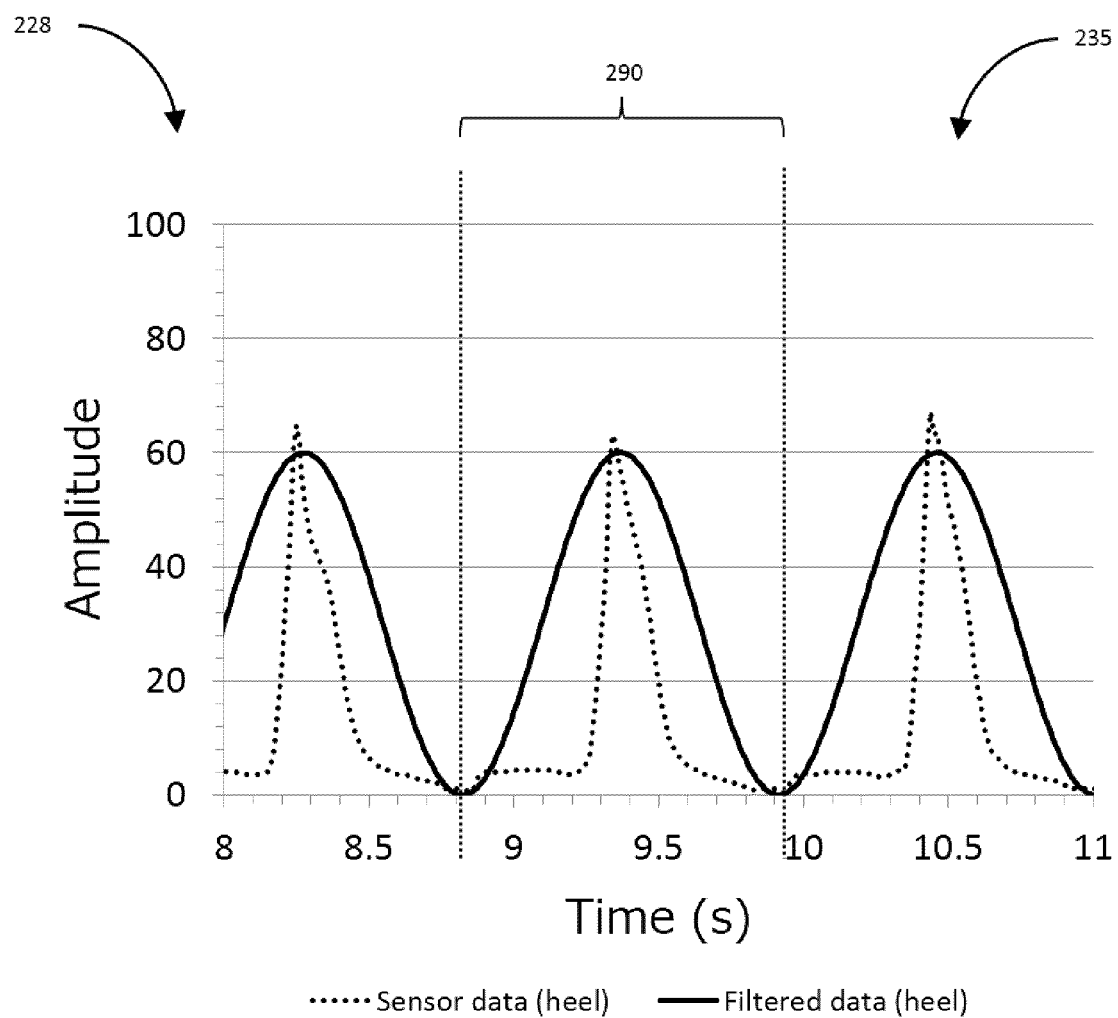
Figure 11E:
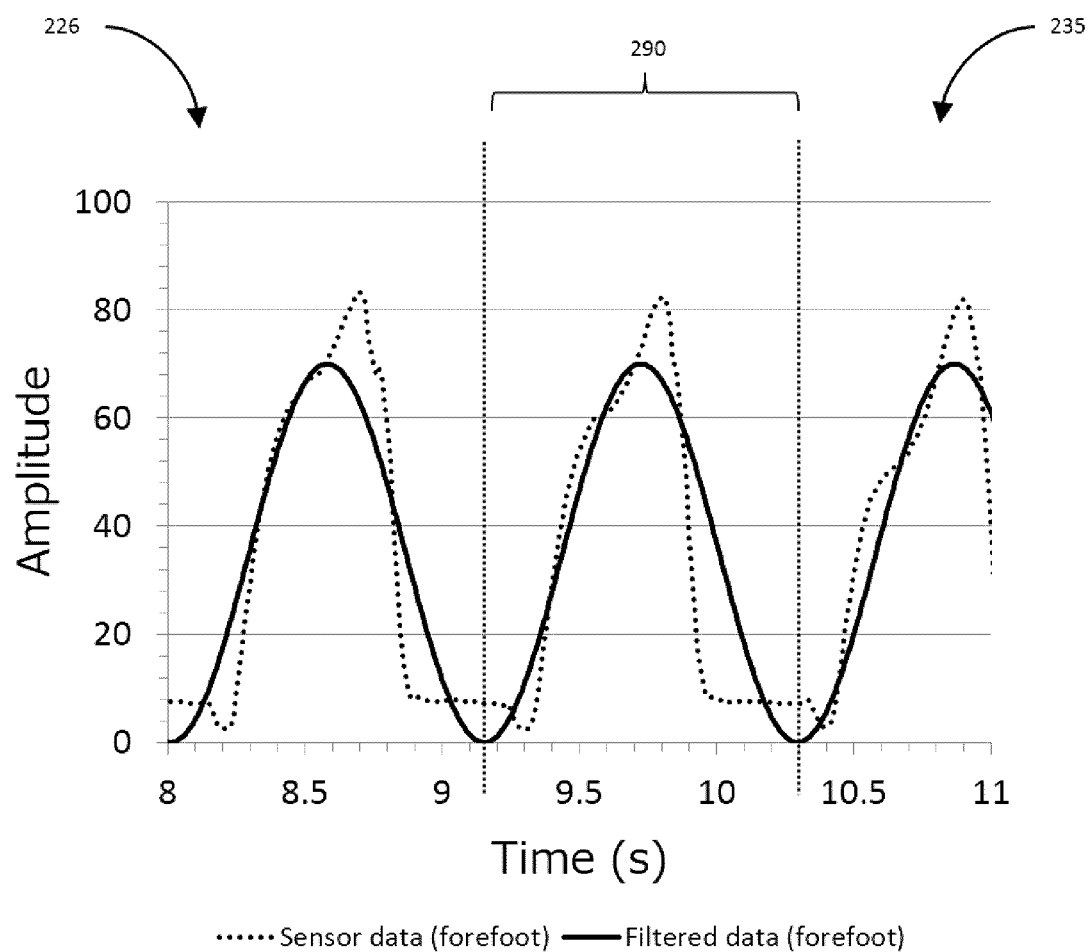

FIGS. 11d and 11e respectively show the sensor data at the heel and at the forefoot (dashed lines), and filtered data 235 at the heel (solid line in FIG. 11d) and the forefoot (solid line in FIG. 11e).

Figure 11F:
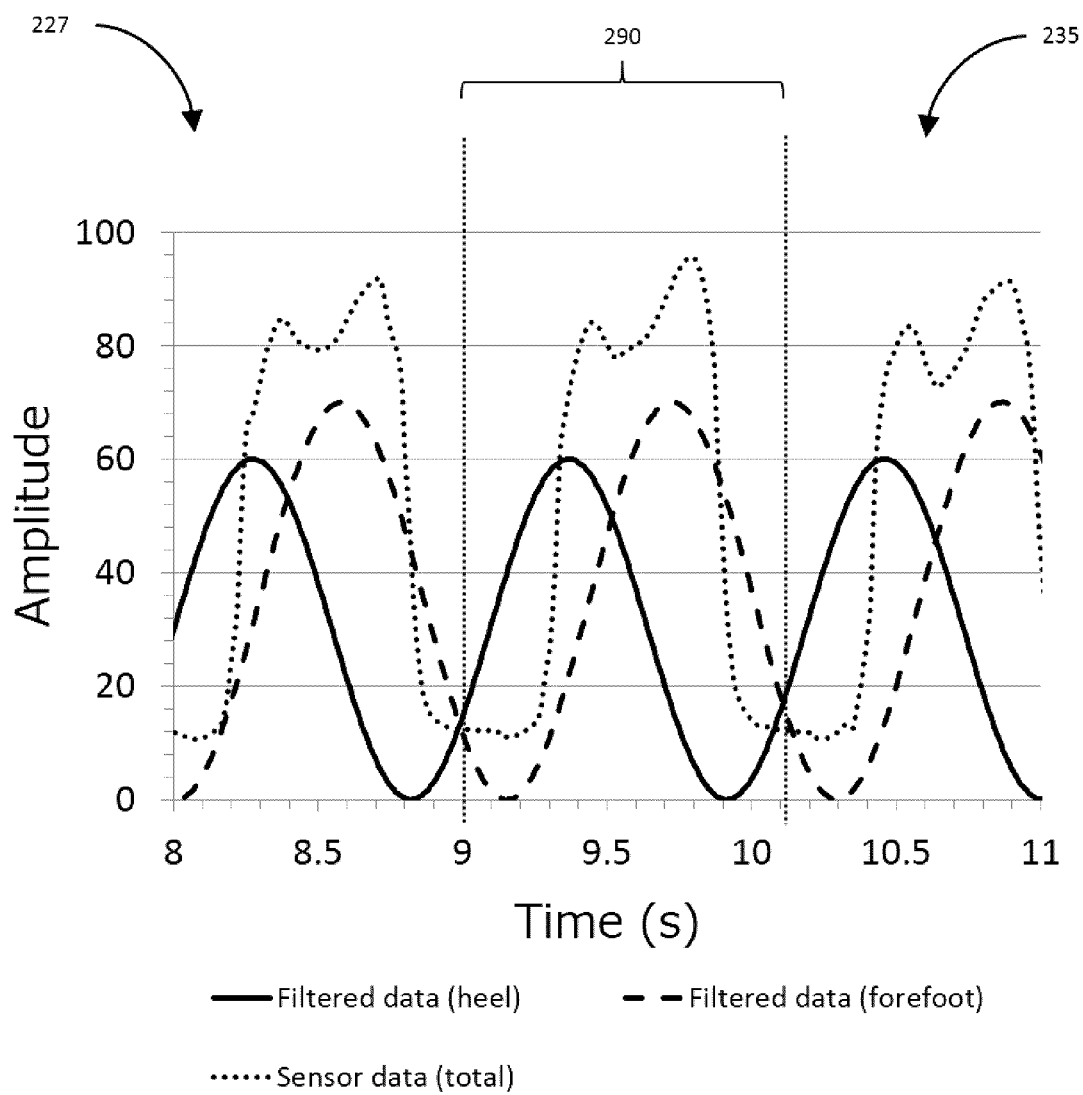

FIG. 11f shows the filtered data 235 at the heel (solid line), the filtered data 235 at the forefoot (dashed line) and the combined sensor data 227 (dotted line). The bounds of the step event 290 are defined at the intersections of the filtered data 235 at the heel (solid line) and the filtered data 235 at the forefoot (dashed line), which correspond to the same points as identified in the summed filtered data 235 prepared from the sensor data 227 of both combined first sensors 222 and second sensor 224.

Figure 12:
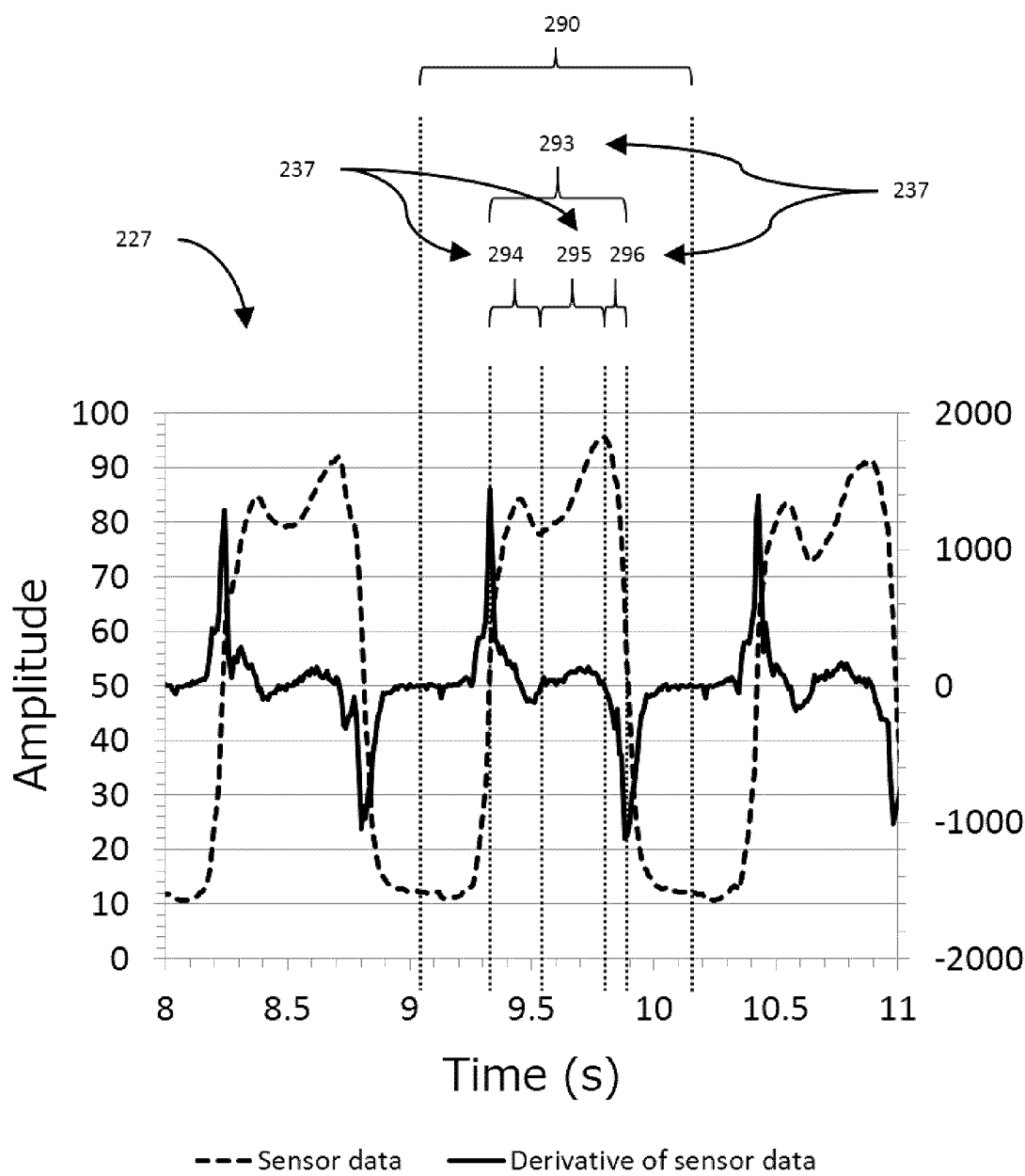
FIG. 12 is a plot of the first derivative of the sensor data of FIG. 9 showing features of an event.

FIG. 12 shows the idealized sensor data 227 (dashed lines) and the derivative of the sensor data 227 (solid line) superimposed with the event bounds of the step event 290 for defining the event data 237. Within the step event 290, a ground contact event 293 may be defined the first derivative of the sensor data 227 (filtered data of the first derivative of the sensor data 227). Once the bounds of the step event 290 are defined using the filtered data 235 of the first derivative of the sensor data 227, similarly to the filtered data 235 of the sensor data 227 in FIGS. 11a to 11f, the ground contact event 293 within the step event 290 may be identified in the first derivative of the sensor data 227.

Underlying the step event 290 is the ground contact event 293. The ground contact event 293 may include a heel strike event 294, a ground contact with the ball of the foot event 295, and a toe-off event 296. Each of the heel strike event 294, ground contact with the ball of the foot event 295, and toe-off foot event 296 are bound by inflection points in the first derivative of the sensor data 227. The inflection points bounding the heel strike event 294 include a local maximum and an inflection point in the derived sensor data 227. The inflection points bounding the ground contact with the ball of the foot event 295 include two inflection points in the derived sensor data 227. The inflection points bounding the toe-off event 296 include an inflection point and a local minimum in the derived sensor data 227.

The simulated sensor data 227 show a well-defined baseline, which facilitates application of a global Fourier transform. In other applications with a drifting baseline, the global Fourier transform may be more likely to result in inaccurate filtering of the time-frequency representation and inaccurate event detection. Similarly, the adaptive localized filtering method may provide additional advantages for applications with a drifting baseline.

FIG. 13 is a schematic of an event detection system 310. The data source 320 includes the first pressure sensor 322 at the heel of an insole, and a second pressure sensor 324 at the forefoot of the insole corresponding to the ball of a foot. Sensor data 327 collected by the data source 320 may then be analyzed by the processing module 330 on the instrumented insole. The event data 337 is the communicated to the to the event data module 340 inside a smart watch. The event data module 340 may transmit the event data 337 to the communication module 342, store the event data 337 in a storage module 344, or both.

Figure 14:
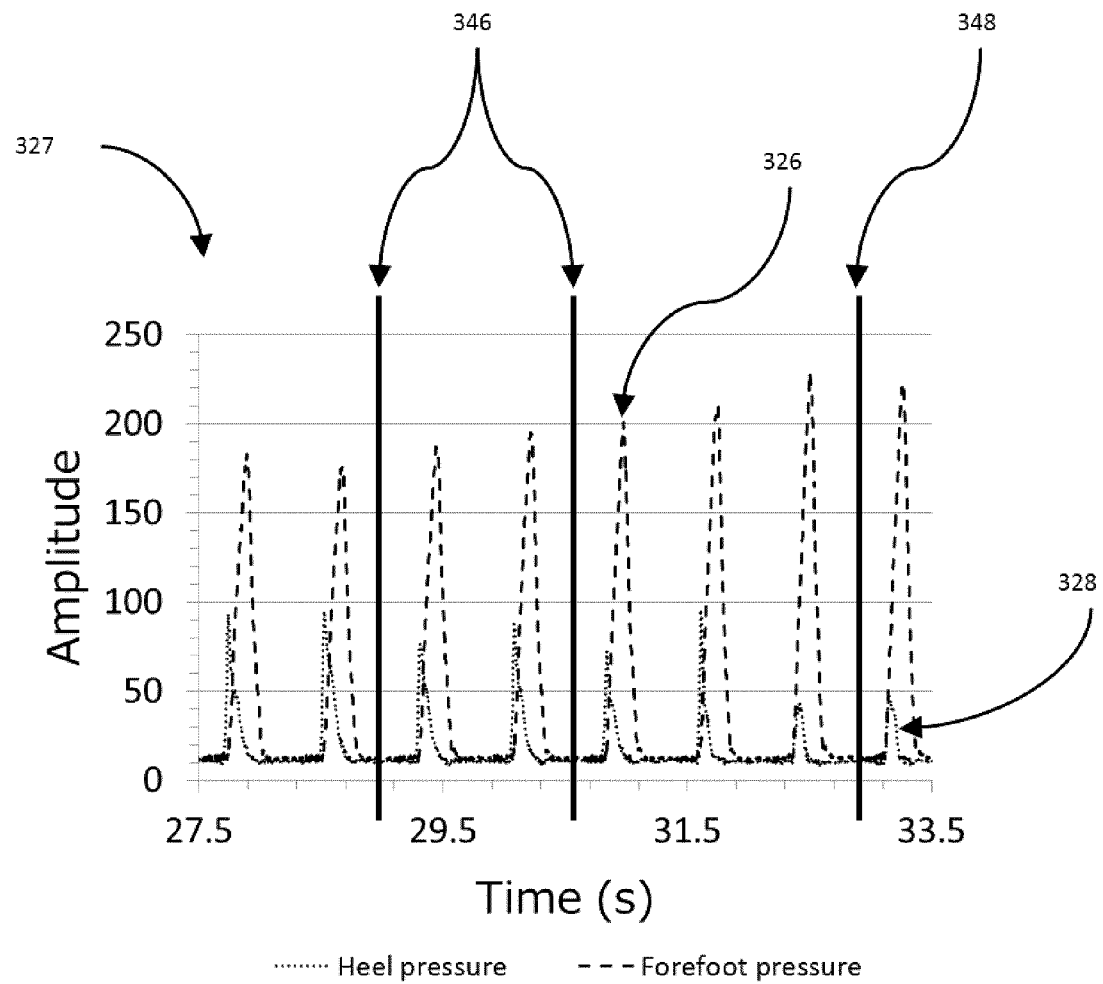
FIG. 14 is a plot of idealized sensor data of the event detection system of FIG. 13.

FIG. 14 depicts idealized sensor data 327 from the event detection system 310. The sensor data 327 includes the first sensor data 326 from the first sensor 322, and the second sensor data 328 from the second sensor 324. Based on the first sensor data 326 and the second sensor data 328 after the bounds of steps are defined by the filtered data, a prompt 346 is provided as voice coaching from the communication module 342 of the event data module 340. The prompt 346 offers suggestions to the user to improve their activity efficiency, mitigate injury or other points. The prompt 346 is a suggestions to move the foot strike zone away from the heel and towards the forefoot in order to minimize joint injury. Two prompts 346 are required before the user changes their behaviour and the heel pressure shown in the second sensor data 328 in decreased. Subsequently, a confirmation 348 is communicated to the user as vibration from the watch, approving of the behavioural change. The below table shows the amplitudes of the heel strikes before and after the prompts 346.

| Time | Amplitude |
|---|---|
| 27.80 | 93.20 |
| 28.52 | 92.45 |
| 29.35 | 73.54 |
| 30.13 | 84.09 |
| 30.88 | 71.35 |
| 31.65 | 97.75 |
| 32.39 | 43.74 |
| 33.14 | 47.90 |

FIG. 15 shows a schematic of an event detection system 410. The data source 420 includes an accelerometer 422 on a footwear insert for a subject individual's foot. The accelerometer 422 could similarly be attached to another part of the shoe, such as on the outside of the tongue, or to another part of the body such as the ankle, shin, thigh, hip, chest, back or shoulder. Acceleration data 427 collected by the accelerometer 422 may then be transmitted by an intermediary storage and transmission device 429, and analyzed by a processing module 430 inside a laptop computer, smart phone, smart watch, server computer or other processing device. The processing device includes an event data module 440. The event data module 440 may communicate the event data 437 to the communication module 442, store the event data 437 to a storage module 444, or both.

Figure 16:
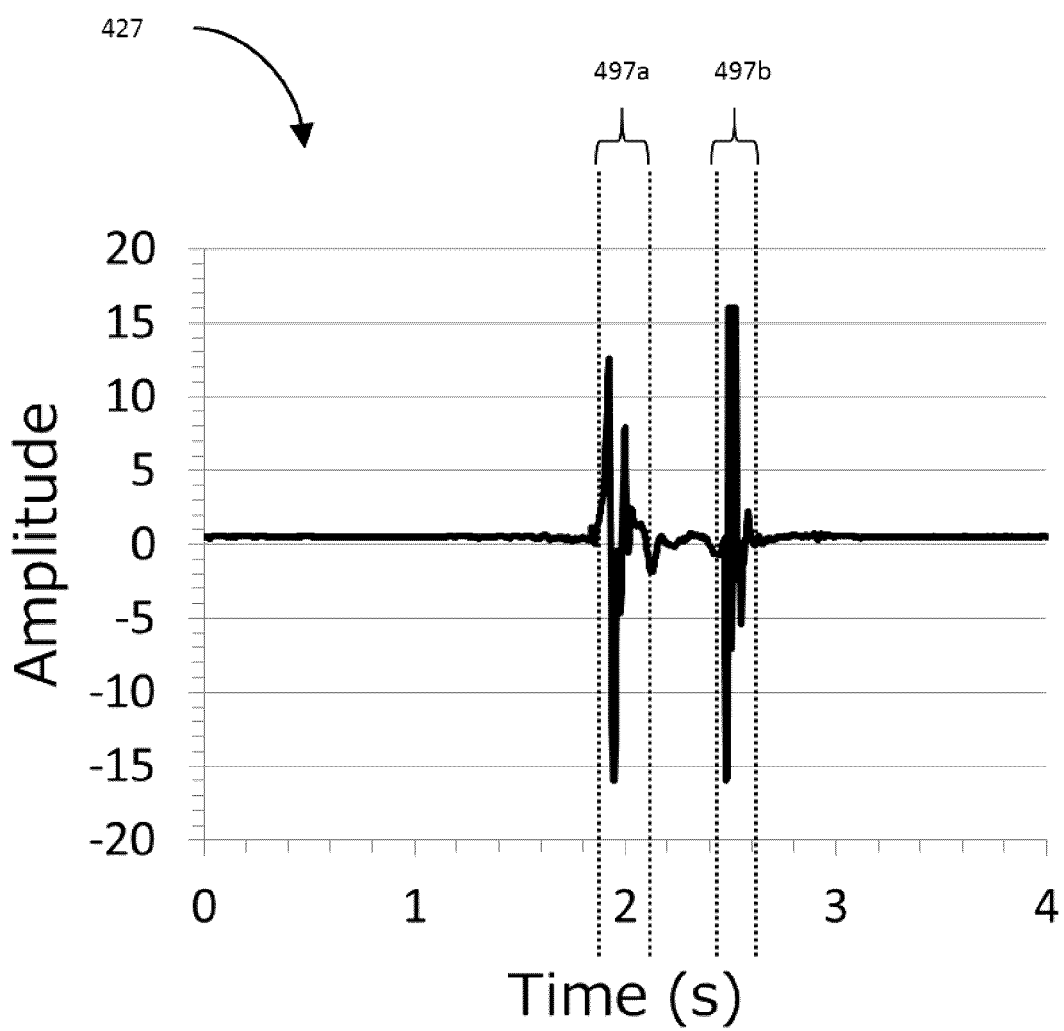
FIG. 16 is a plot of idealized sensor data of the event detection system of FIG. 15.

FIG. 16 is an example plot of sensor data 427 based on the sensor data 427 from an accelerometer 422 in FIG. 13. The sensor data 427 represents a user jumping and landing back on the ground. Events 490 may be distinguished within the sensor data 427, corresponding to takeoff and landing of the user, which elicit spikes in acceleration. The events 490 illustrate non-repetitive events.

Figure 17:
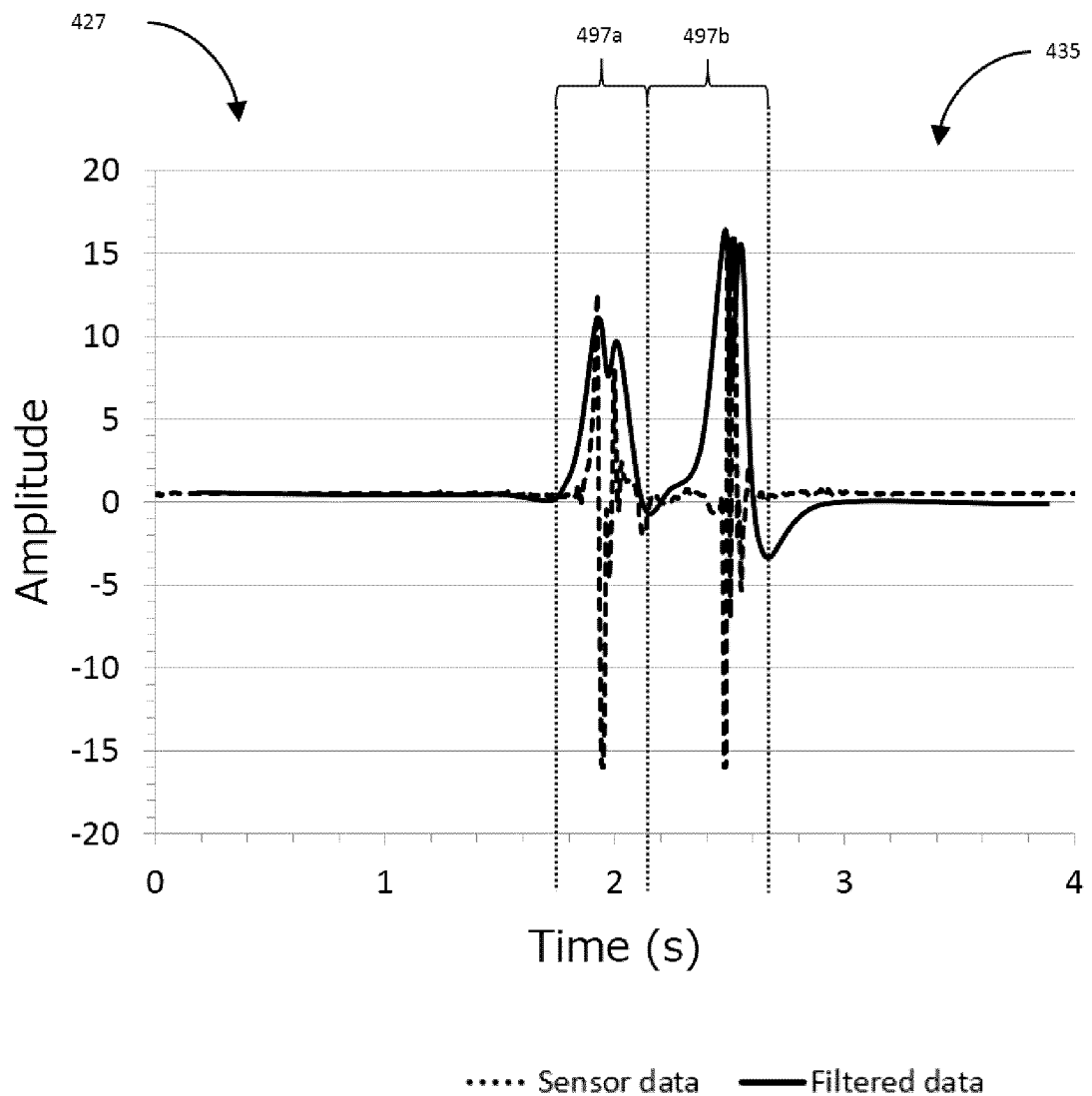
FIG. 17 is a plot of idealized filtered sensor data of the event detection system of FIG. 15.

FIG. 17 is a plot of filtered data 435 (solid lines) based on the sensor data 427 of FIG. 14 (dashed lines). Two jumping events 497a and 497b are characterized by the bounds of the filtered data 435 through the adaptive localized filter process (e.g. the localized filtering method 60 or the localized filtering method 160) by identifying inflection points within the filtered data. In this case, the events are respectively the accelerations associated with the takeoff and landing of a jumping motion.

Figure 18:
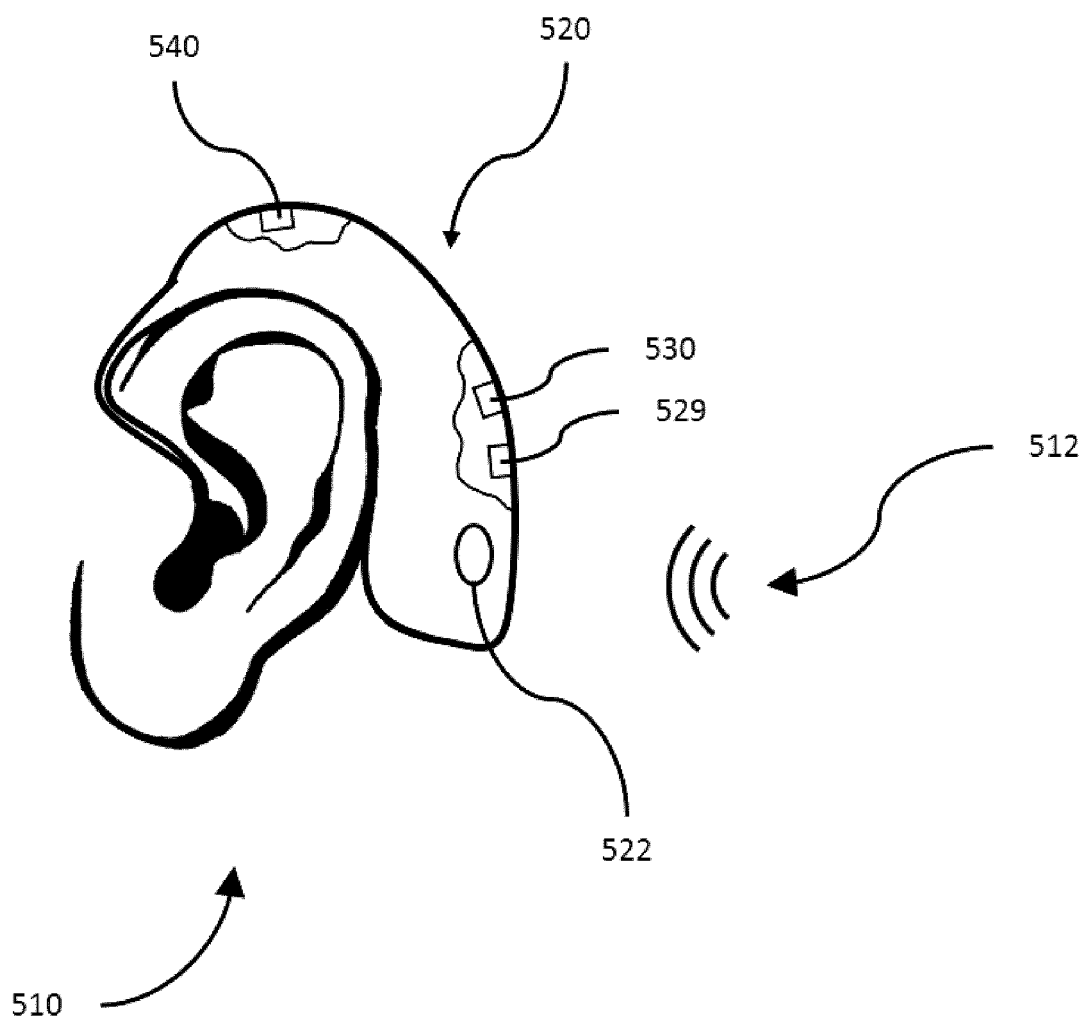
FIG. 18 shows an event detection system.

FIG. 18 is a schematic of an event detection system 510. In this embodiment, the system is a hearing aid, with built-in capability to take in environmental noise, and select an appropriate filter in order to provide a suitable signal to the user's ear. The data source 520 includes a microphone 522 that records noises 512 from the user's environment as sound signals 527. The sound signal 527 is the transmitted by an intermediary storage and transmission device 529 to a processing module 530 within the hearing aid. The processing module 530 produces event data which is passed to the event data module 540 where it is communicated to the communication module 542. The communication module may then pass along a modified noise signal to the user, filtered according to the event data.

Figure 19:
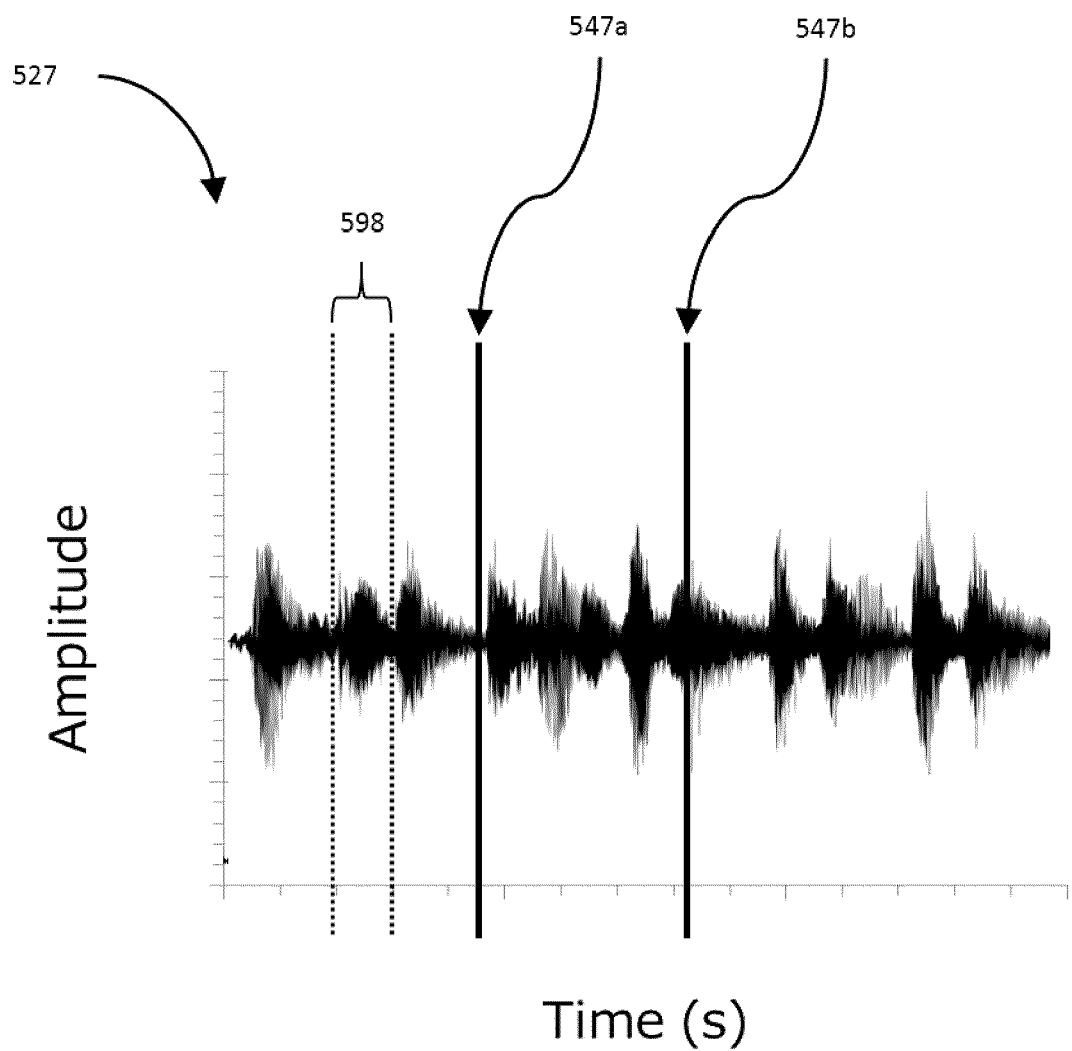
FIG. 19 is a plot of idealized sensor data of the event detection system of FIG. 18.

FIG. 19 is an example plot of sensor data 527 based on the hearing aid event detection system 510 of FIG. 18. The sensor data 527 represents environmental noise (e.g. talking, music, etc.). Events 590 may be distinguished within the sensor data 527 and passed on to an event data module 540 as event data.

Figure 20:
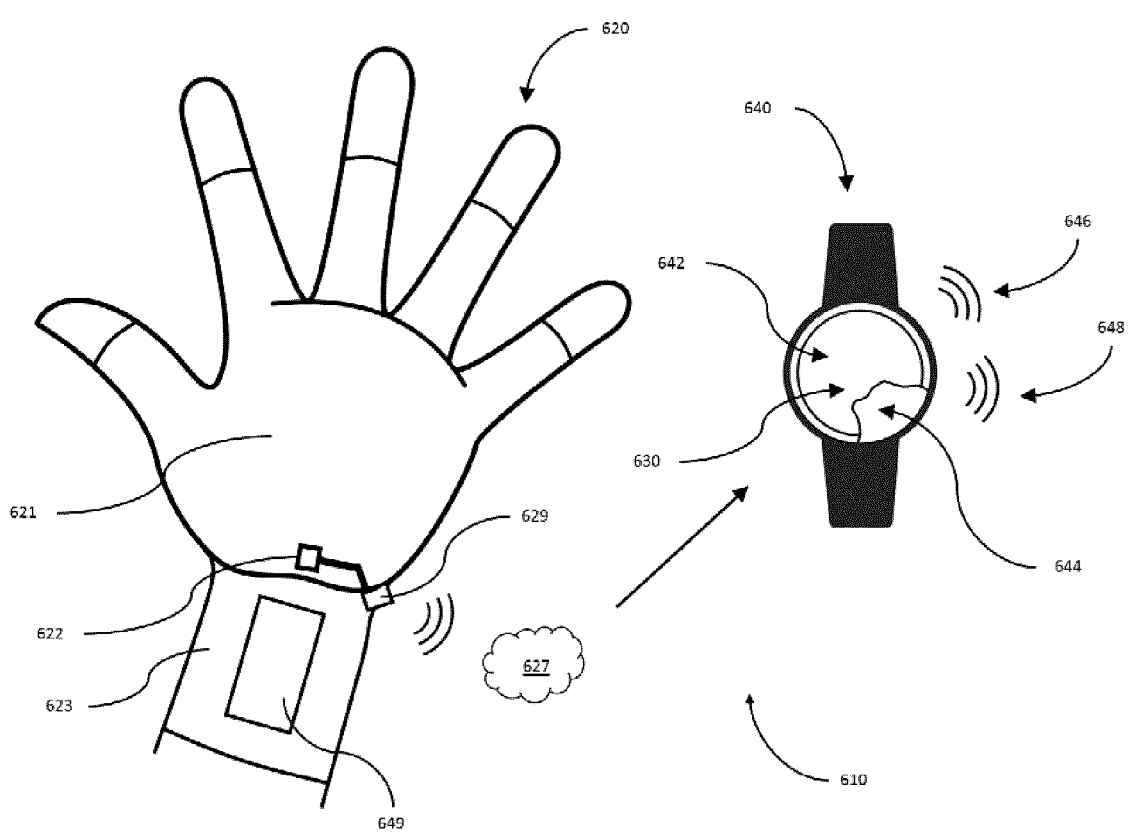
FIG. 20 shows an event detection system.

FIG. 20 is a schematic of an event detection system 610. An accelerometer 622 sits at the base of the palm of an instrumented glove 621. Sensor data 627 collected by the accelerometer 622 is then transmitted by an intermediary storage and transmission device 629, and analyzed by a processing module 630 inside a processing module 630, in this case, a smart watch. The processed event data 637 is communicated to the event data module 640, where it may be passed to a communication module 66 or stored by a storage module 644. The communication module may communicate an event, such as wrist flexion large enough to cause high internal pressures in the carpal tunnel and resulting nerve damage, to a user through audio, vibratory, or visual cues. The glove 621 includes variable stiffness material 649 in a wrist portion 623 of the glove 621 for correcting carpal tunnel inducing behavior, and the stiffness may be adjusted as a parameter of the system 610 such as at defining parameters 151 of the method 150. The accelerometer-as-a-level may also be referred to as "inclination sensing" using the accelerometer 622.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method for detecting heterogeneous events comprising:
    receiving pressure sensor data;
    defining a data window over a time period of the pressure sensor data;
    calculating a time-frequency representation of the data window for providing the time-frequency representation corresponding to the time period;
    calculating a filter mask based on the time-frequency representation, wherein the filter mask comprises non-binary values proportional to a positive exponent of a magnitude of a time-frequency transform, wherein more prominent frequencies will be emphasized, and less prominent frequencies will be de-emphasized;
    filtering the time-frequency representation with the filter mask, providing filtered data;
    identifying features in the filtered data;
    identifying a body movement event with reference to the features; and
    outputting the body movement event.

2. The method of claim 1 wherein the pressure sensor data comprises at least two different types of data.

3. The method of claim 1 wherein the method further comprises receiving data of acceleration, rotation, seismic changes, temperature, humidity, and/or sound.

4. The method of claim 1 wherein receiving the pressure sensor data is at a down-sampled rate to increase body movement event detection speed.

5. The method of claim 1 wherein the data window includes a first data window from which the pressure sensor data is received, and a second data window from which the filtered data is provided, and receiving the pressure sensor data of the first data window is at a rate determined with reference to the filtered data of the second data window, the second data window preceding the first data window in time.

6. The method of claim 1 wherein the time period of the data window has a duration equal to additional data windows preceding or succeeding the data window.

7. The method of claim 1 wherein calculating the time-frequency representation of the data window comprises applying an S-transform to the pressure sensor data within the data window.

8. The method of claim 1 wherein calculating the time-frequency representation of the data window comprises applying a Gabor transform to the pressure sensor data within the data window.

9. The method of claim 1 wherein filtering the time-frequency representation comprises normalizing all values in the time-frequency representation.

10. The method of claim 1 wherein the features comprise inflection points.

11. The method of claim 1 wherein identifying the body movement event comprises deriving an event count or defining the features as endpoints of the body movement event.

12. The method of claim 11 wherein identifying the body movement event comprises characterizing the pressure sensor data between time points corresponding to the endpoints defined in the filtered data.

13. The method of claim 1 wherein identifying the body movement event comprises defining a pulse width, a cycle, a ground contact time, a center of pressure, or a path of center of pressure of the pressure sensor data or the filtered data.

14. The method of claim 1 wherein outputting the body movement event comprises communicating data relating to the body movement event to an individual, prompting the individual to change a health-based behavior with event feedback, storing data relating to the body movement event in a computer readable medium, or outputting contribution to the pressure sensor data from each of a plurality of sensors.

15. A system for detecting heterogeneous events comprising:
    a sensor for receiving sensor data; and
    a processor in communication with the sensor for receiving the sensor data;
    wherein the processor is configured to execute instructions for carrying out the method of claim 1.

16. The system of claim 15 wherein the processor is configured for localized filtering of the time-frequency representation based on the filter mask by applying an S-transform to the sensor data.

17. The system of claim 15 wherein the sensor comprises a pressure sensor and one or more of a gyroscope, an accelerometer, a seismograph, a thermometer, or a humidity sensor.

18. The system of claim 15 wherein the sensor is configured to monitor activities, movements, and functions of a wearer of the sensor.

19. The system of claim 15 wherein the sensors are mounted on a shoe insert.

* * * * *